United States Patent
Deno et al.

(10) Patent No.: US 10,194,994 B2
(45) Date of Patent: Feb. 5, 2019

(54) SYSTEMS AND METHODS FOR ORIENTATION INDEPENDENT SENSING

(71) Applicant: St. Jude Medical, Cardiology Division, Inc., St. Paul, MN (US)

(72) Inventors: D. Curtis Deno, Andover, MN (US); Ram K. Balachandran, Maple Grove, MN (US); Stéphane Massé, Toronto (CA)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 38 days.

(21) Appl. No.: 15/152,496

(22) Filed: May 11, 2016

(65) Prior Publication Data

US 2016/0331471 A1  Nov. 17, 2016

Related U.S. Application Data

(60) Provisional application No. 62/160,376, filed on May 12, 2015.

(51) Int. Cl.
*A61B 5/05* (2006.01)
*A61B 34/20* (2016.01)
(Continued)

(52) U.S. Cl.
CPC ........ *A61B 34/20* (2016.02); *A61B 5/04017* (2013.01); *A61B 5/0422* (2013.01);
(Continued)

(58) Field of Classification Search
CPC ............... A61B 34/20; A61B 18/1492; A61B 2017/00053; A61B 2018/00648;
(Continued)

(56) References Cited

U.S. PATENT DOCUMENTS

| 4,649,924 A | 3/1987 | Taccardi |
| 5,297,549 A | 3/1994 | Beatty et al. |

(Continued)

FOREIGN PATENT DOCUMENTS

| EP | 1166714 | 1/2002 |
| EP | 1336379 | 8/2003 |

(Continued)

OTHER PUBLICATIONS

Liu, Tu-Ying et al.; "Functional Characterization of the Crista Terminalis in Patients with Atrial Flutter: Implications of Radiofrequency Ablation"; JACC; vol. 43; No. 9; pp. 1639-1645; May 5, 2004.

(Continued)

*Primary Examiner* — George Manuel
(74) *Attorney, Agent, or Firm* — Dykema Gossett PLLC

(57) ABSTRACT

A system and method for obtaining an OIS coordinate frame comprising an electronic control unit configured to determine a local 3D electric field loop, create a zero mean version of E(t) over a depolarization interval, compute an $\dot{E}$ value at each of a plurality of time intervals, compute an initial estimate of $\hat{w}$ from a cross product of E and the $\dot{E}$ value for each of the plurality of time intervals, average the initial estimate of $\hat{w}$ from each of the plurality of time for a best estimate of $\hat{w}$, determine a plurality of $\hat{a}(\theta)$ values and using the corresponding $\hat{n}(\theta)$ values, compute a composite match score, and choose at least one best value for $\hat{a}$ and a best value for $\hat{n}$.

20 Claims, 18 Drawing Sheets

(51) Int. Cl.
*A61B 5/00* (2006.01)
*A61B 5/042* (2006.01)
*A61B 18/14* (2006.01)
*A61B 5/04* (2006.01)
A61B 18/00 (2006.01)
A61B 90/00 (2016.01)
A61B 17/00 (2006.01)

(52) U.S. Cl.
CPC .......... *A61B 5/6858* (2013.01); *A61B 5/7221* (2013.01); *A61B 18/1492* (2013.01); *A61B 2017/00053* (2013.01); *A61B 2018/00267* (2013.01); *A61B 2018/00577* (2013.01); *A61B 2018/00648* (2013.01); *A61B 2034/2053* (2016.02); *A61B 2090/064* (2016.02)

(58) Field of Classification Search
CPC ...... A61B 2034/2053; A61B 2090/064; A61B 5/04017; A61B 5/0422; A61B 5/6858; A61B 5/7221; A61B 2018/00267; A61B 2018/00577
See application file for complete search history.

(56) References Cited

U.S. PATENT DOCUMENTS

| | | | |
|---|---|---|---|
| 5,848,972 | A | 12/1998 | Triedman et al. |
| 5,921,923 | A | 7/1999 | Kuck et al. |
| 6,233,476 | B1 | 5/2001 | Strommer et al. |
| 6,360,121 | B1 | 3/2002 | Shoda et al. |
| 6,400,981 | B1 | 6/2002 | Govari |
| 6,498,944 | B1 | 12/2002 | Ben-Haim et al. |
| 6,546,270 | B1 | 4/2003 | Goldin et al. |
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 8,862,213 | B2 | 10/2014 | Lo et al. |
| 8,876,817 | B2 | 11/2014 | Avitall |
| 2006/0253030 | A1* | 11/2006 | Altmann ............... A61B 5/042 600/466 |
| 2007/0225589 | A1 | 9/2007 | Viswanathan |
| 2008/0221643 | A1 | 9/2008 | Olson |
| 2009/0248014 | A1 | 10/2009 | Shachar et al. |
| 2010/0168557 | A1 | 7/2010 | Deno et al. |
| 2010/0168560 | A1 | 7/2010 | Hauck et al. |
| 2013/0190747 | A1 | 7/2013 | Koblish et al. |
| 2013/0274582 | A1 | 10/2013 | Afonso et al. |
| 2014/0058375 | A1 | 2/2014 | Koblish |
| 2014/0336518 | A1 | 11/2014 | Shuros et al. |

FOREIGN PATENT DOCUMENTS

| | | |
|---|---|---|
| EP | 2186474 | 5/2010 |
| JP | 11047148 A | 2/1999 |
| JP | 2001061789 | 3/2001 |
| JP | 2002-051998 | 2/2002 |
| JP | 2007537831 A | 12/2007 |
| JP | 2012524606 A | 10/2012 |
| WO | 1997/024983 | 7/1997 |
| WO | 2012/037471 | 3/2012 |
| WO | 2012/092016 | 7/2012 |
| WO | 2014/113612 | 7/2014 |
| WO | 2014/182822 | 11/2014 |

OTHER PUBLICATIONS

Masse, M. et al.; "Velocity Field Analysis of Activation Maps in Atrial Fibrillation a Simulation Study"; World Congress on Medical Physics and Biomedical Engineering; vol. 25/4; pp. 1014-1017; Sep. 2009.

Mazeh, Nachaat et al.; "A Simplified Approach for Simultaneous Measurements of Wavefront Velocity and Curvature in the Heart Using Activation Times"; Cardiovascular Engineering and Technology; vol. 4; No. 4; Dec. 2013.

Michaud, Gregory F. et al.; "Information at our Catheter Tips: Unipolar Electrogram Morphology Makes another Comeback!"; Heart Rhythm; vol. 7; No. 9; pp. 1301-1302; Sep. 2010.

Mironov, Sergey et al.; "Role of Conduction Velocity Restitution and Short-Term Memory in the Development of Action Potential Duration Alternans in Isolated Rabbit Hearts"; Circulation; pp. 17-25; Jul. 1, 2008.

Mountantonakis, Stavros E. et al.; "Relationship between Voltage Map "Channels" and the Location of Critical Isthmus Sites in Patients with Post-Infarction Cardiomyopathy and Ventricular Tachycardia"; JACC; vol. 61; No. 20; pp. 2088-2095; May 21, 2013.

Nanthakumar, Kumaraswamy et al.; "Regional Differences in Ventricular Fibrillation in the Open-Chest Porcine Left Ventricle": Circulation Research; pp. 734-740; Oct. 18, 2002.

Narayan, Sanjiv M. et al.; "Treatment of Atrial Fibrillation by the Ablation of Localized Sources"; JACC; vol. 60; No. 7; pp. 628-636; Aug. 14, 2012.

Nayyar, Sachin et al.; "High-Density Mapping of Ventricular Scar a Comparison of Ventricular Tachycardia (VT) Supporting Channels with Channels that do not Support VT"; Circulation; pp. 90-98; Feb. 2014.

Otomo, Kiyoshi et al.; "Local Unipolar and Bipolar Electrogram Criteria for Evaluating the Transmurality of Atrial Ablation Lesions at Different Catheter Orientations Relative to the Endocardial Surface"; Heart Rhythm; vol. 7; No. 9; pp. 1291-1300; Sep. 2010.

Parson, Ian D. et al.; "Cardiac Mapping Instrumentation for the Instantaneous Display of Endocardial and Epicardial Activation"; IEEE Transactions on Biomedical Engineering; vol. BME-34; No. 6; pp. 468-472; Jun. 1987.

Patel, Parin J. et al.; "Electroanatomic Mapping of the Intercaval Bundle in Atrial Fibrillation"; Circulation; pp. 1262-1267, Dec. 2014.

Pieper, Carl F. et al.; "Simultaneously Collected Monopolar and Discrete Bipolar Electrograms: Comparison of Activation Time Detection Algorithms"; PACE; vol. 16; pp. 426-433; Mar. 1993.

Plank, G. et al.; "Cardiac Near-Field Morphology During Conduction Around a Microscopic Obstacle—a Computer Simulation Study"; Annals of Biomedical Engineering; vol. 31; No. 10; pp. 1206-1212; Nov. 2003.

Plank, G. et al.; "Model Study of Vector-Loop Morphology During Electrical Mapping of Microscopic Conduction in Cardiac Tissue"; Annals of Biomedical Engineering; vol. 28; No. 10; pp. 1244-1252; Oct. 2000.

Plank, G. et al.; "Use of Cardiac Electric Near-Field Measurements to Determine Activation Times"; Annals of Biomedical Engineering; vol. 31; No. 9; pp. 1066-1075; Oct. 2003.

Price, Adam et al.; "Novel Ablation Catheter Technology that Improves Mapping Resolution and Monitoring of Lesion Maturation"; The Journal of Innovations in Cardiac Rhythm Management; pp. 599-609; Jan. 2012.

Ravelli, Flavia et al.; "Wave Similarity Mapping Shows the Spatiotemporal Distribution of Fibrillatory Wave Complexity in the Human Right Atrium During Paroxysmal and Chronic Atrial Fibrillation"; Journal of Cardiovascular Electrophysiology; vol. 16; No. 10; pp. 1071-1076; Oct. 2005.

Rogers, Jack M. et al.; "Quantitative Techniques for Analyzing High-Resolution Cardiac-Mapping Data"; IEEE Engineering in Medicine and Biology; vol. 17, No. 1; pp. 62-72; Jan. 1, 1998.

Schilling, Richard J. et al.; "Simultaneous Endocardial Mapping in the Human Left Ventricle Using a Noncontact Catheter"; Circulation; pp. 887-898; Sep. 1, 1998.

Schmitt, Otto H. et al.; "Symposium on Electrocardiography and Vectorcardiography the Present Status of Vectorcardiography", JAMA Internal Medicine; vol. 96; No. 5; pp. 574-590; Nov. 1955.

Schuler. S. et al.; "Influence of Catheter Orientation, Tissue Thickness and Conduction Velocity on the Intracardiac Electrogram"; Biomedizinische Technik/Biomedical Engineering; Sep. 2013.

(56) References Cited

OTHER PUBLICATIONS

Schumacher, Burghard et al.; "Transverse Conduction Capabilities of the Crista Terminalis in Patients with Atrial Flutter and Atrial Fibrillation"; JACC; vol. 34., No. 2; pp. 363-373; Aug. 1999.

Shors, Stephanie M. et al. "A method for Determining High-Resolution Activation Time Delays in Unipolar Cardiac Mapping"; IEEE Transactions on Biomedical Engineering; vol. 43; No. 12; pp. 1192-1196; Dec. 1996.

Spears, Danna A. et al.; "Relationship of Bipolar and Unipolar Electrogram Voltage to Scar Transmurality and Composition Derived by Magnetic Resonance Imaging in Patients with Nonischemic Cardiomyopathy Undergoing VT Ablation"; Heart Rhythm; vol. 9; No. 11; pp. 1837-1846; Nov. 2012.

Stevenson, William G. et al.; "Recording Techniques for Clinical Electrophysiology"; Journal of Cardiovascular Electrophysiology; vol. 16; No. 9; pp. 1017-1022; Sep. 2005.

Tedrow, Usha B. et al.; "Recording and Interpreting Unipolar Electrograms to Guide Catheter Ablation"; Heart Rhythm; vol. 8; No. 5; pp. 791-796; May 2011.

Thompson, Nathaniel C. et al.; "Improved Spatial Resolution and Electrogram Wave Direction Independence with the Use of an Orthogonal Electrode Configuration" J Clin Monit Comput; pp. 157-163; Apr. 2014.

Tungjitkusolmun, Supan et al.; "Guidelines for Predicting Lesion Size at Common Endocardial Locations During Radio-Frequency Ablation"; IEEE Transactions on Biomedical Engineering; vol. 48; No. 2; pp. 194-201, Feb. 2001.

Weber, Frank M. et al.; "Conduction Velocity Restitution of the Human Atrium—An Efficient Measurement Protocol for Clinical Electrophysiological Studies"; IEEE Transactions on Biomedical Engineering; vol. 58; No. 9; pp. 2648-2655; Sep. 2011.

Weber, Frank M. et al.; "Wave-Direction and Conduction-Velocity Analysis from Intracardiac. Electrograms—a Single-Shot Technique"; IEEE Transactions on Biomedical Engineering; vol. 57; No. 10; pp. 2394-2401; Oct. 2010.

Witkowski, Francis X. et al.; "In Vivo Estimation of Cardiac Transmembrane Current"; Circulation Research; vol. 72; No. 2; pp. 424-439; Feb. 1993.

Yamada, Takumi et al.; "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation"; Heart Rhythm, vol. 3; No. 4; pp. 377-384; Apr. 2006.

Yamada, Takumi; "Pulmonary Vein isolation with a Multielectrode Basket Cather"; Indian Pacing and Electrophysiology Journal; pp. 97-109; Apr. 2007.

Zaman, Junaid, A.B, et al.; "The Rotor Revolution Conduction at the Eye of the Storm in Atrial Fibrillation"; Circulation; pp. 1230-1236; Dec. 2014.

Zhang, Xin et al.; "Noninvasive Three-Dimensional Electrocardiographic Imaging of Ventricular Activation Sequence"; AJP-Heart Circ Physical; vol. 289; pp. H2724-H2732; Aug. 5, 2005.

Anter, Elad et al.; High-Resolution Mapping of Scar-Related Atrial Arrhythmias Using Smaller Electrodes with Closer Interelectrode Spacing; Circulation; vol. 8; No. 3, Jun. 2015.

Arora, Rishi et al.; "Fundamentals of Intracardiac Mapping", Catheter Ablation of Cardiac Arrhythmias; pp. 107-134, 2006.

Avitall, Boaz et al.; "Maximal Electrogram Attenuation Recorded from Mini Electrodes Embedded on 4.5-mm Irrigated and 8-mm Nonirrigated Catheters Signifies Lesion Maturation"; Journal of Cardiovascular Electrophysiology; vol. 26; No. 2; Feb. 2015.

Balasundaram, Krishnanand et al.; "Tracking Rotors with Minimal Electrodes: Modulation Index Based Strategy"; Circulation; vol. 8; No. 2; Apr. 2015.

Barnette, AR et al.; "Estimation of a 3-D Conduction Velocity Vector Fields from Cardiac Mapping Data"; Computers in Cardiology; vol. 25; pp. 605-608; Sep. 1998.

Bayly, Philip V. et al.; "Estimation of Conduction Velocity Vector Fields from Epicardial Mapping Data"; IEEE Transactions on Biomedical Engineering; vol. 45; No. 5; pp. 563-569; May 1998.

Bayly, PV et al.; "Estimation of Conduction Velocity Vector Fields from 504-Channel Epicardial Mapping Data"; Computers in Cardiology; pp. 133-136; Sep. 1996.

Banharash, Peyman et al.; "Quantitative Analysis of Localized Sources Identified by Focal Impulse and Rotor Modulation Mapping in Atrial Fibrillation"; Circulation; pp. 554-561; Jun. 2015.

Bharati, Saroja et al.; "The Conduction System of the Swine Heart"; Chest; vol. 100; No. 1; pp. 207-212; Jul. 1991.

Bortone, Agustin et al.; "Unipolar Signal Modification as a Guide for Lesion Creation During Radiofrequency Application in the Left Atrium Prospective Study in Humans in the Setting of Paroxysmal Atrial Fibrillation Catheter Ablation"; Circulation; pp. 1096-1102; Dec. 2013.

Bouman, L.N. et al.; "Structure and Function of the Sino-Atrial Node: A Review"; European Heart Journal; vol. 7; No. 2; pp. 94-104; Feb. 1986.

Boyett, M.R. et al.; "The Sinoatrial Node, a Heterogeneous Pacemaker Structure"; Cardiovascular Research; vol. 47; No. 4; Sep. 2000.

Burch, George E. et al.; "Chapter X The Development of Spatial Vectrocardioaraphy"; A History of Electrocardiography; Norman Publishing; pp. 235-248; Apr. 1990.

Cantwell, C.D. et al., "Techniques for Automated Local Activation Time Annotation and Conduction Velocity Estimation in Cardiac Mapping"; Computers in Biology and Medicine; Oct. 1, 2015.

Casella, Michela et al.; "Feasibility of Combined Unipolar and Bipolar Voltage Maps to Improve Sensitivity of Endomycardial Biopsy"; Circulation; Jun. 2015.

Chan, Rodrigo C. et al.; "The Effect of Ablation Length and Catheter Tip to Endocardial Orientation on Radiofrequency Lesion Size in the Canine Right Atrium"; PACE; vol. 25; No. 1; Jan. 2002.

Damle, Roger S.; "Atrial and Accessory Pathway Activation Direction in Patients with Orthodromic Supraventricular Tachycardia: Insights from Vector Mapping" JACC; vol. 23; No. 3; pp. 684-692; Mar. 1, 1994.

De Bakker, Jacques M.T. et al.; "The Pathophysiologic Basis of Fractionated and Complex Electrograms and the Impact of Recording Techniques on Their Detection and Interpretation"; Circulation; vol. 3, No. 2; Apr. 2010.

De Bakker, Jacquest M.T. et al.; "Activation Mapping: Unipolar Versus Bipolar Recording"; Cardiac Electrophysiology from Cell to Bedside Second Edition; pp. 1068-1078; Jan. 28, 1995.

Deng, Dong-dong et al.; "Simulation of Biatrial Conduction via Different Pathways during Sinus Rhythm with a Detailed Human Atrial Model"; Journal of Zhjiang University—Science B (Biomedicine & Biotechnology); pp. 676-694; Sep. 2012.

Deng, Dongdong at al.; "An Image-Based Model of the Whole Human Heart with Detailed Anatomical Structure and Fiber Orientation", Compuutational and Mathematical Methods in Medicine; vol. 2012; Jul. 2012.

Desai, Jawahar M. et al.; "Two Phase Radiofrequency Catheter Ablation of Isolated Ventricular Endomyocardium"; PACE, vol. 14; pp. 1179-1194; Jul. 1991.

Dubois; R. et al.; "Global and Directional Activation Maps for Cardiac Mapping in Electrophysiology"; Computing in Cardiology; pp. 349-352; Sep. 2012.

Fees; Luca et al.; "A Method for Quantifying Atrial Fibrillation Organization Based on Wave-Morphology Similarity"; IEEE Transactions on Biomedical Engineering; vol. 49; No. 12; pp. 1504-1513; Dec. 2002.

Fedotov, N.M. et al.; "Methods for Increasing the Reliability of Coordinate Determination by the Location and Imaging Systems of Endocardial Electrodes"; Biomedical Engineering; vol. 41, No. 4; pp. 145-149; Jul. 1, 2007.

Fisher, Westby G. et al.; "Three-Dimensional Electrogram Mapping Improves Ablation of Left-Sided Accessory Pathways"; PACE; vol. 15; pp. 2344-2356; Dec. 1992.

Fitzgerald, Tamara N. et al.; "Comparative Psychometric Analysis of Vector and Isochrone Cardiac Activation Maps"; IEEE Transactions on Biomedical Engineering; vol. 51; No. 5; pp. 847-855; May 2004.

(56) References Cited

OTHER PUBLICATIONS

Fitzgerald, Tamara N. et al.; "Estimation of Cardiac Conduction Velocities Using Small Data Sets"; Annals of Biomedical Engineering; vol. 31; pp. 250-261, Mar. 2003.

Fitzgerald, Tamara N. et al.; "Identification of Cardiac Rhythm Features by Mathematical Analysis of Vector Fields"; IEEE Transactions on Biomedical Engineering; vol. 52; No. 1; pp. 19-29; Jan. 2005.

Gaudette, RJ et al.; "Epicardial Velocity Estimation Using Wavelets"; Computers in Cardiology; vol. 24; pp. 339-342; Sep. 7, 1997.

Gerstenfeld, Edward P. et al.; "Detection of Changes in Atrial Endocardial Activation with Use of an Orthogonal Catheter"; JACC; vol. 18; No. 4; pp. 1034-1042; Oct. 1991.

Gerstenfeld, Edward P. et al.; "Evidence for Transient Linking of Atrial Excitation During Atrial Fibrillation in Humans"; Circulation; vol. 86; No. 2; pp. 375-382; Aug. 1992.

Gornick, Charles C. et al.; "Validation of a New Noncontact Catheter System for Electroanatomic Mapping of Left Ventricular Endocardium"; Circulation; pp. 829-835; Feb. 16, 1999.

Gupta, Sanjaya at al.; "Rapid Ablation of Recurrent Atrial Flutter Using a Novel Ablation Catheter": The Journal of Innovations in Cardiac Rhythm Management; No. 5; pp. 1808-1812; Nov. 2014.

Haddad, El et al.; "Novel Algorithmic Methods in Mapping of Atrial and Ventricular Tachycardia"; Circulation; Jun. 2014.

Harrild, David M. et al.; "A Computer Model of Normal Conduction in the Human Atria"; Circulation Research; Sep. 29, 2000.

Horner, S.M. et al.; "Electrode for Recording Direction of Activation, Conduction Velocity, and Monophasic Action Potential of Myocardium"; The American Physiological Society; pp. H1917-H1927; Apr. 1997.

Huang, Jian et al.; "Evolution of the Organization of Epicardial Activation Patterns During Ventricular Fibrillation"; Journal of Cardiovascular Electrophysiology; vol. 9, No. 12; Dec. 1998.

Ideker, Raymond E. et al.; "The Assumptions of Isochronal Cardiac Mapping"; PACE; vol. 12; pp. 456-478; Mar. 1989.

Irie, Tadanobu et al.; "Relationship Between Sinus Rhythm Late Activation Zones and Critical Sites for Scar-Related Ventricular Tachycardia: a Systematic Analysis of Isochronal Late Activation Mapping"; Circulation; Apr. 2015.

Kadish, Alan et al..; "Mapping of Atrial Activation with a Noncontact, Multielectrode Catheter in Dogs"; Circulation; pp. 1906-1913; Apr. 13, 1999.

Kadish, Alan H. et al.; "Vector Mapping of Myocardial Activation"; Circulation; vol. 74; No. 3; pp. 603-615 Sep. 1986.

Karney, Charles F.F. et al.; "Quaternions in Molecular Modeling"; Journal of Molecular Graphics and Modeling; pp. 595-804; Jan. 2007.

Kay, Matthew W. et al.; "Measuring Curvature and Velocity Vector Fields for Waves of Cardiac Excitation in 2-D Media"; IEEE Transactions on Biomedical Engineering; vol. 52; No. 1; pp. 50-63; Jan. 2005.

Kearsley, Simon K.; "On the Orthogonal Transformation Used for Structural Comparisons"; Acta Crystallographica Section A; A45; pp. 208-210; Feb. 1, 1989.

Kumar, Saurabh et al; "Unipolar Electrogram Morphology to Assess Lesion Formation During Catheter Ablation of Atrial Fibrillation Successful Translation into Clinical Practice"; Circ Arrhythm Electrophysiol; pp. 1050-1052; Dec. 2013.

Kumar, Saurabh et al.; "Unipolar Electrogram Morphology to Assess Lesion Formation During Catheter Ablation of Atrial Fibrillation Successful Translation into Clinical Practice"; Circulation; pp. 1050-1052; Dec. 2013.

Lindsay, Bruce D., et al.; "Novel Directional Activation Map Using Local Propagation Between Adjacent Electrograms"; Heart Rhythm; vol. 8; No, 5; May 2011 Supplement.

Liu, Chenguang et al.; "Three-Dimensional Imaging of Ventricular Activation and Electrograms from Intracavity Recordings"; IEEE Transactions on Biomedical Engineering; vol. 58; No. 4; pp. 868-875; Apr. 2011.

\* cited by examiner

SYSTEMS AND METHODS FOR ORIENTATION INDEPENDENT SENSING

CROSS-REFERENCE TO RELATED APPLICATIONS

This application claims the benefit of U.S. provisional application No. 62/160,376, filed 12 May 2015, which is hereby incorporated by reference as though fully set forth herein.

BACKGROUND a. Field

This disclosure relates to systems, apparatuses and methods for utilizing electrode spatial arrangements within a mapping system. In particular, the instant disclosure relates to systems, apparatuses and methods for characterizing cardiac conduction conditions in a catheter orientation independent manner using electrode spatial arrangements in 3D mapping systems.

b. Background

Electrophysiology (EP) catheters are used in a variety of diagnostic, therapeutic, and/or mapping and ablative procedures to diagnose and/or correct conditions such as atrial or ventricular arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. This lesion disrupts undesirable cardiac activation pathways and thereby limits, corrals, or prevents errant conduction signals that can form the basis for arrhythmias.

To position a catheter at a desired site within the body, some type of navigation may be used, such as using mechanical steering features incorporated into the catheter (or a sheath). In some examples, medical personnel may manually manipulate and/or operate the catheter using the mechanical steering features.

A navigating system may be used for visualization and to facilitate the advancement of catheters through a patient's vasculature to specific locations within the body. Such navigating systems may include, for example, electric and/or magnetic field based positioning and navigating systems that are able to determine the position and orientation of the catheter (and similar devices) within the body.

Conduction disorders in the body can result from abnormal conduction in regions as small as 1-4 mm. In addition, ablation in these regions must be restricted to the pathological tissue to preserve electrical and mechanical function, particularly with ventricular arrhythmias. Today, many catheters employ electrode pairs spaced greater than 4 mm apart which can make it difficult to reliably allow discrimination or localization of defects. Even when the electrodes are more closely spaced, around 1 mm to around 2 mm, the orientation of the pair of electrodes is a prominent factor in the amplitude and morphology of the resulting signals.

The foregoing discussion is intended only to illustrate the present field and should not be taken as a disavowal of claim scope.

BRIEF SUMMARY

In one embodiment, a system for obtaining an OIS coordinate frame comprises an electronic control unit configured to determine a local 3D electric field loop, create a zero mean version of E(t) over a depolarization interval, compute an $\dot{E}$ value at each of a plurality of time intervals, compute an initial estimate of $\hat{w}$ from a cross product of E and the $\dot{E}$ value for each of the plurality of time intervals, average the initial estimate of $\hat{w}$ from each of the plurality of time for a best estimate of $\hat{w}$, determine a plurality of $\hat{a}(\theta)$ values and choosing a corresponding $\hat{n}(\theta)$ value for each of the plurality of $\hat{a}(\theta)$ values, compute a composite match score, and choose at least one best value for $\hat{a}$ and a best value for $\hat{n}$.

In another embodiment, a method for obtaining an OIS coordinate frame comprises determining a local 3D electric field loop, creating a zero mean version of E(t) over a depolarization interval, computing an $\dot{E}$ value at each of a plurality of time intervals, computing an initial estimate of $\hat{w}$ from a cross product of E and the $\dot{E}$ value for each of the plurality of time intervals, averaging the initial estimate of $\hat{w}$ from each of the plurality of time for a best estimate of $\hat{w}$, determining a plurality of $\hat{a}(\theta)$ values and choosing a corresponding $\hat{n}(\theta)$ value for each of the plurality of $\hat{a}(\theta)$ values, computing a composite match score, and choosing at least one best value for $\hat{a}$ and a best value for $\hat{n}$.

In yet another embodiment, a system for obtaining an OIS coordinate frame comprises an electronic control unit configured to determine a local 3D electric field loop, compute a composite match score for how well $\varphi$ matches an inner product of E and $\hat{a}(\theta)$ and $-\varphi$ matches an inner product of E and $\hat{n}$, choose a best value for $\hat{a}$ and a best value for $\hat{n}$, and determine a value for $\hat{w}$ by a right hand rule and a cross product $\hat{w} = \hat{n} \times \hat{a}$.

DETAILED DESCRIPTION

Cardiac EP mapping today primarily uses bipolar electrograms (EGMs) obtained from electrode pairs. Bipoles are preferred as they have reduced low frequency noise, reduced far-field effects and often produce sharp and well-recognized features when filtered appropriately. Unipolar EGMs on the other hand contain far-field information and less stable baselines that make them less attractive for mapping purposes. A feature of the unipolar signal that makes it useful for mapping is the fact that its morphology and amplitude are independent of catheter orientation. Amplitudes and morphology of bipolar EGM's are dependent on the orientation of the electrode pair from which they are calculated and hence depend on the orientation of the catheter. The dependence on orientation results in inconsistently measured amplitudes and morphology-based measurements like activation times. It therefore also impacts derived quantities like scar boundaries, activation direction, and conduction velocity.

Electrophysiologic information may also be elicited by pacing a tissue or organ and observing the resulting spread of depolarization from immediately adjacent to the site where capture occurs. These observations are difficult with current technology because of pacing artifacts but directional information provided by $E_n$, $E_a$, or v, as described herein, can serve as clues to anatomic or functional conduction blocks. Even without pacing, conduction around obstacles such as valve orifices or blocks is known to become curved and slowed and this can be directly mapped and visualized with the information disclosed herein much more conveniently and reliably than previously possible.

Figure 1A:
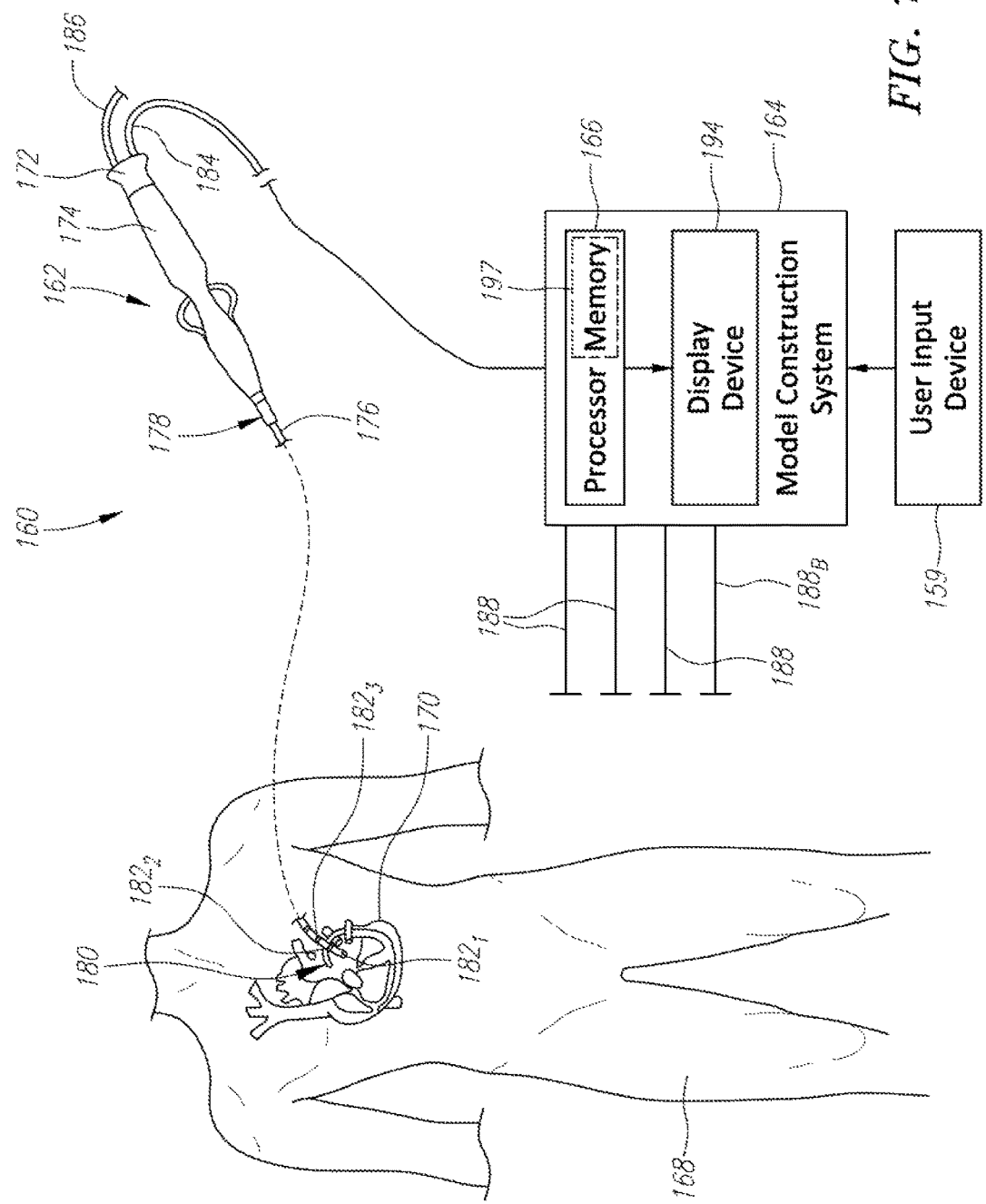
FIG. 1A is a diagrammatic view of a system for generating surface models and/or mapping electrophysiological information thereon.

FIG. 1A illustrates one embodiment of a system 160 for mapping electrophysiological information corresponding to an anatomic structure onto a multi-dimensional (e.g., three-dimensional) geometry surface model of the anatomic structure (each of the terms "electrophysiology" and "electrophysiological" will hereinafter be referred to as "EP"). The system 160 comprises, among other components, a medical device 162 and a model construction system 164. In one embodiment, the medical device 162 comprises a catheter, and the model construction system 164 comprises, in part, a processing apparatus 166. The processing apparatus 166 may take the form of an electronic control unit, for example, that is configured to obtain a geometry surface model of the cardiac structure, and to construct an EP map corresponding to the cardiac structure using data collected by, for example, the catheter 162. The catheter 162 is configured to be inserted into a patient's body 168, and more particularly, into the patient's heart 170. The catheter 162 may include a cable connector or interface 172, a handle 174, a shaft 176 having a proximal end 178 and a distal end 180 and one or more sensors 182 (e.g., $182_1$, $182_2$, $182_3$) mounted in or on the shaft 176 of the catheter 162. In one embodiment, the sensors 182 are disposed at or near the distal end 180 of the shaft 176. The connector 172 provides mechanical, fluid, and electrical connection(s) for cables, such as, for example, cables 184, 186 extending to the model construction system 164 and/or other components of the system 160 (e.g., a visualization, navigation, and/or mapping system (if separate and distinct from the model construction system 164), an ablation generator, irrigation source, etc.).

The sensors 182 mounted in or on the shaft 176 of the catheter 162 are electrically connected to the model construction system 164, and the processing apparatus 166 thereof, in particular. The sensors 182 may be provided for a variety of diagnostic and therapeutic purposes including, for example and without limitation, EP studies, pacing, cardiac mapping, and ablation. In an embodiment, one or more of the sensors 182 are provided to perform a location or position sensing function. Accordingly, in such an embodiment, as the catheter 162 is moved along a surface of the cardiac structure and/or about the interior thereof, the sensor(s) 182 can be used to collect location data points that correspond to the surface of, or locations within, the cardiac structure. These location data points can then be used by, for example, the model construction system 164 in the construction of a geometry surface model of the cardiac structure.

In one embodiment, the model construction system 164, and the processing apparatus 166 thereof, in particular, is configured to obtain a geometry surface model of the cardiac surface (or at least a portion thereof), and to map EP information corresponding to that cardiac structure onto the geometry surface model. The processing apparatus 166 is configured to use, at least in part, data (location data and/or EP data/information) collected by the catheter 162 in the construction of one or both of a geometry surface model and an EP map.

In an embodiment wherein the model construction system 164 is configured to construct the geometry surface model, the model construction system 164 is configured to acquire location data points collected by the sensor(s) 182 corresponding to the cardiac structure. The model construction system 164 is configured to then use those location data points in the construction of the geometry surface model of the cardiac structure. The model construction system 164 is configured to construct a geometry surface model based on some or all of the collected location data points. In addition to constructing a geometry surface model of a structure, the model construction system 164 is configured to function with the sensor(s) 182 to collect location data points that are used in the construction of the geometry surface model. In such an embodiment, the model construction system 164 may comprise an electric field-based system, such as, for example, the EnSite NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other exemplary embodiments, however, the model construction system 164 may comprise other types of systems, such as, for example and without limitation: a magnetic-field based system such as the Carto™ System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster.

In one embodiment, the sensor(s) 182 of the catheter 162 comprise positioning sensors. The sensor(s) 182 produce signals indicative of catheter location (position and/or orientation) information. In an embodiment wherein the model construction system 164 is an electric field-based system, the sensor(s) 182 may comprise one or more electrodes. In such an embodiment, each of the electrodes may comprise one of a number of types of electrodes, such as, for example, tip electrodes, ring electrodes, button electrodes, coil electrodes, brush electrodes, flexible polymer electrodes, and spot electrodes. Alternatively, in an embodiment wherein the model construction system 164 is a magnetic field-based system, the sensor(s) 182 may comprise one or more magnetic sensors configured to detect one or more characteristics of a low-strength magnetic field. For instance, in one exemplary embodiment, the sensor(s) 182 may comprise magnetic coils disposed on or in the shaft 176 of the catheter 162.

For purposes of clarity and illustration, the model construction system 164 will hereinafter be described as comprising an electric field-based system, such as, for example, the EnSite NavX™ system identified above. It will be appreciated that while the description below is primarily limited to an embodiment wherein the sensor(s) 182 comprise one or more electrodes, in other exemplary embodiments, the sensor(s) 182 may comprise one or more magnetic field sensors (e.g., coils). Accordingly, model construction systems that include positioning sensor(s) other than the sensors or electrodes described below remain within the spirit and scope of the present disclosure.

Figure 1B:
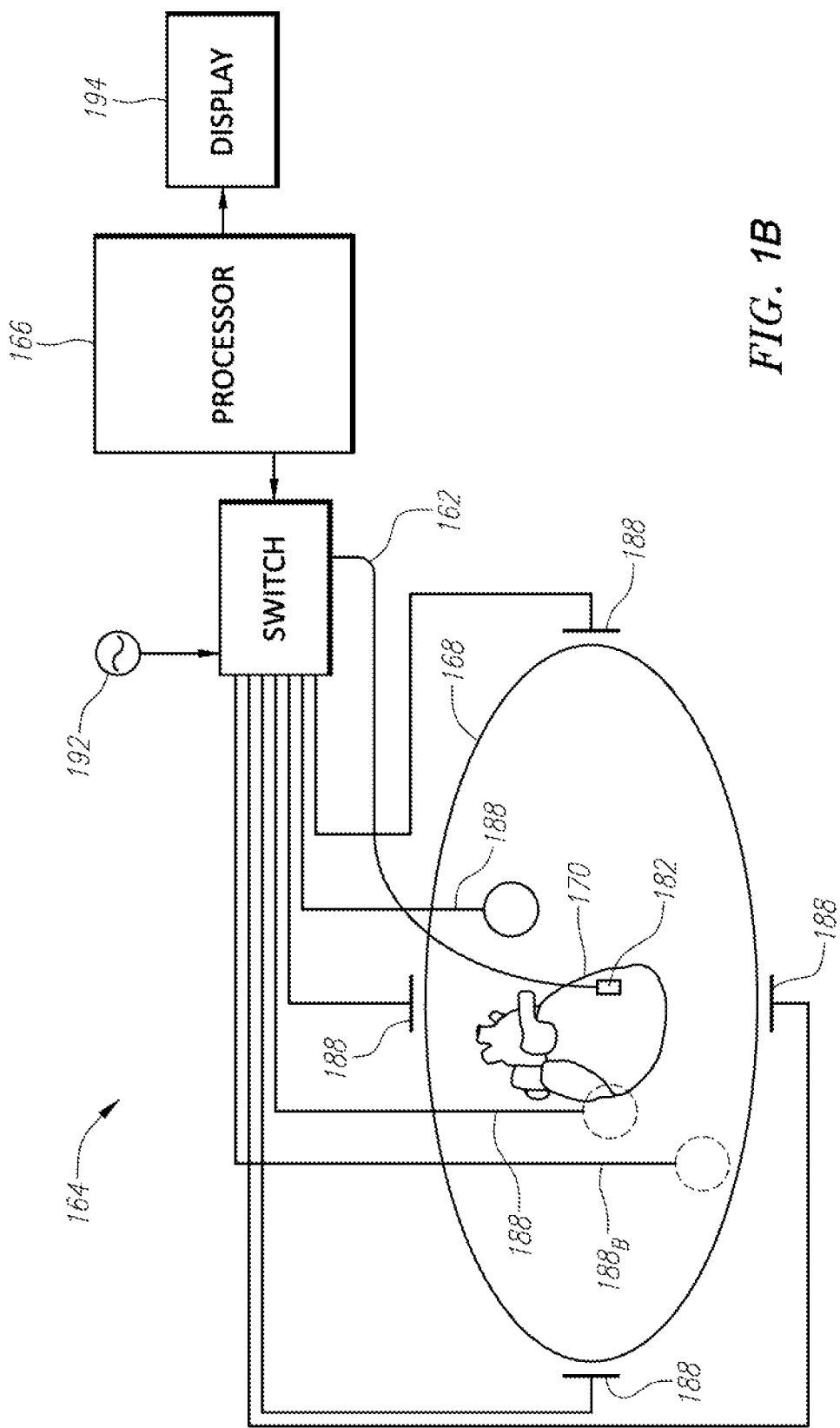
FIG. 1B is simplified diagrammatic and schematic view of a model construction system of the system illustrated in FIG. 1A.

With reference to FIG. 1B, in addition to the processing apparatus 166, the model construction system 164 may include, among other possible components, a plurality of patch electrodes 188, a multiplex switch 190, a signal generator 192, and a display device 194. In another exemplary embodiment, some or all of these components are separate and distinct from the model construction system 164 but that are electrically connected to, and configured for communication with, the model construction system 164.

The processing apparatus 166 may comprise a programmable microprocessor or microcontroller, or may comprise an application specific integrated circuit (ASIC). The processing apparatus 166 may include a central processing unit (CPU) and an input/output (I/O) interface through which the processing apparatus 166 may receive a plurality of input signals including, for example, signals generated by patch electrodes 188 and the sensor(s) 182, and generate a plurality of output signals including, for example, those used to control and/or provide data to, for example, the display device 194 and the switch 190. The processing apparatus 166 may be configured to perform various functions, such as those described in greater detail above and below, with appropriate programming instructions or code (i.e., software). Accordingly, the processing apparatus 166 is programmed with one or more computer programs encoded on a computer storage medium for performing the functionality described herein.

With the exception of the patch electrode 188B called a "belly patch," the patch electrodes 188 are provided to generate electrical signals used, for example, in determining the position and orientation of the catheter 162. In one embodiment, the patch electrodes 188 are placed orthogonally on the surface of the body 168 and are used to create axes-specific electric fields within the body 168.

In one embodiment, the sensor(s) 182 of the catheter 162 are electrically coupled to the processing apparatus 166 and are configured to serve a position sensing function. More particularly, the sensor(s) 182 are placed within electric fields created in the body 168 (e.g., within the heart) by exciting the patch electrodes 188. For purposes of clarity and illustration only, the description below will be limited to an embodiment wherein a single sensor 182 is placed within the electric fields. It will be appreciated, however, that in other exemplary embodiments that remain within the spirit and scope of the present disclosure, a plurality of sensors 182 can be placed within the electric fields and then positions and orientations of each sensor can be determined using the techniques described below.

When disposed within the electric fields, the sensor 182 experiences voltages that are dependent on the location between the patch electrodes 188 and the position of the sensor 182 relative to tissue. Voltage measurement comparisons made between the sensor 182 and the patch electrodes 188 can be used to determine the location of the sensor 182 relative to the tissue. Accordingly, as the catheter 162 is swept about or along a particular area or surface of interest, the processing apparatus 166 receives signals (location information) from the sensor 182 reflecting changes in voltage levels on the sensor 182 and from the non-energized patch electrodes 188. Using various known algorithms, the processing apparatus 166 may then determine the location (position and orientation) of the sensor 182 and record it as a location data point corresponding to a location of the sensor 182 on the surface of, or within, the cardiac structure in a memory or storage device associated with, or accessible, by the processing apparatus 166, such as the memory 197. In one embodiment, prior to recording the location as a location data point, the raw location data represented by the signals received by the processing apparatus 166 may be corrected by the processing apparatus 166 to account for respiration, cardiac activity, and other artifacts using known or hereafter developed techniques. The system described in FIGS. 1A and 1B is further described in U.S. application Ser. No. 14/533,630, filed 5 Nov. 2014, which is hereby incorporated by reference as though fully set forth herein.

One aspect described herein addresses a unique way to combine the benefit of orientation independence of the unipolar signals with the other benefits of bipolar signals that were highlighted previously. The disclosure utilizes closely spaced electrodes on high-density diagnostic catheters to derive local "pseudo bipolar", "equivalent bipole", or "omnipolar" signals that are catheter orientation independent and are free of low-frequency noise and far-field effects. The closely spaced electrodes can be located on a single high-density diagnostic or other catheter or in some embodiments can be located on multiple catheters where electrodes on the catheters are located near or adjacent each other. Furthermore, the equivalent bipolar EGMs so derived possess characteristic shapes and relationships that reflect physiologic and anatomic directions which enable better contact maps by virtue of more consistent activation timing directions. The presence of closely spaced electrodes also helps to characterize the substrate in the immediate vicinity (e.g., a few mm) of the catheter. The omnipolar electrogram signal's amplitude and morphology would only be a function of the local substrate's electrophysiology and hence lends itself to the creation of better, consistent, and more useful contact maps. Examples of high-density catheters that can be used for the purpose include (but are not limited to) the catheters shown in FIG. 2, and basket catheters like the catheters shown in FIG. 3 and FIG. 7.

Figure 2A:
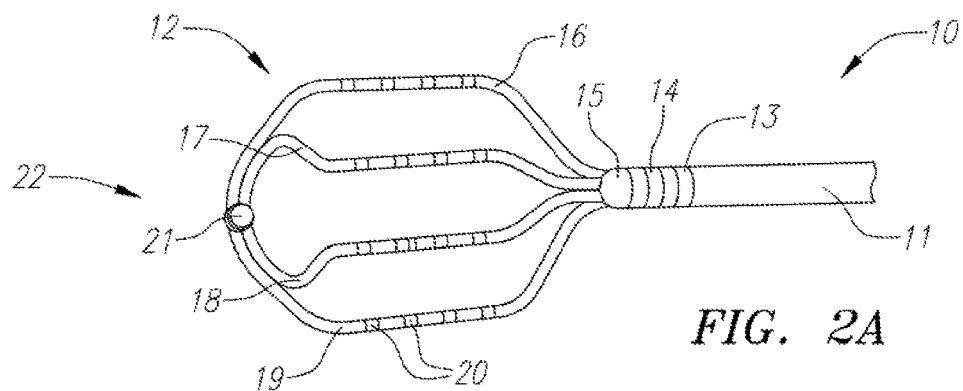
FIG. 2A is an isometric view of one embodiment of a paddle catheter.
Figure 2B:
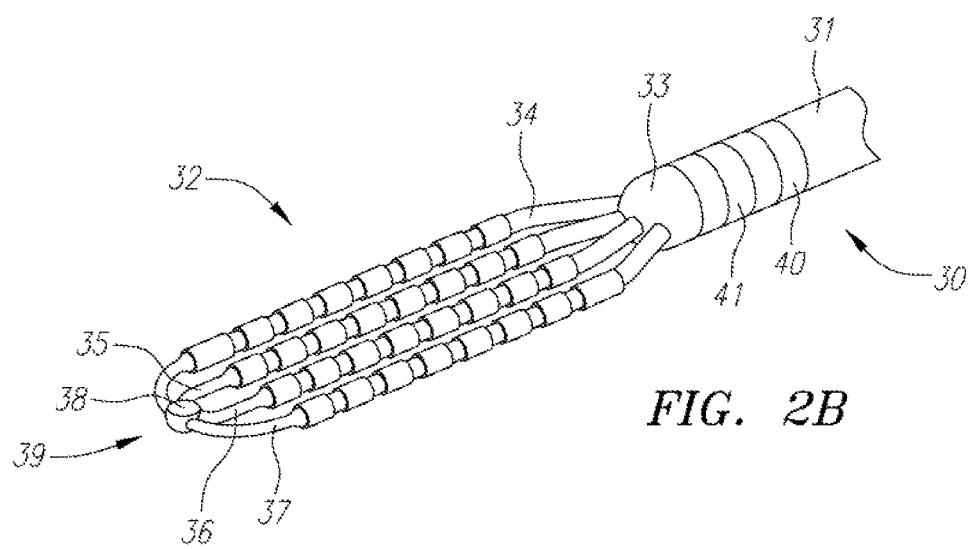
FIG. 2B is an isometric view of another embodiment of a paddle catheter.
Figure 2C:
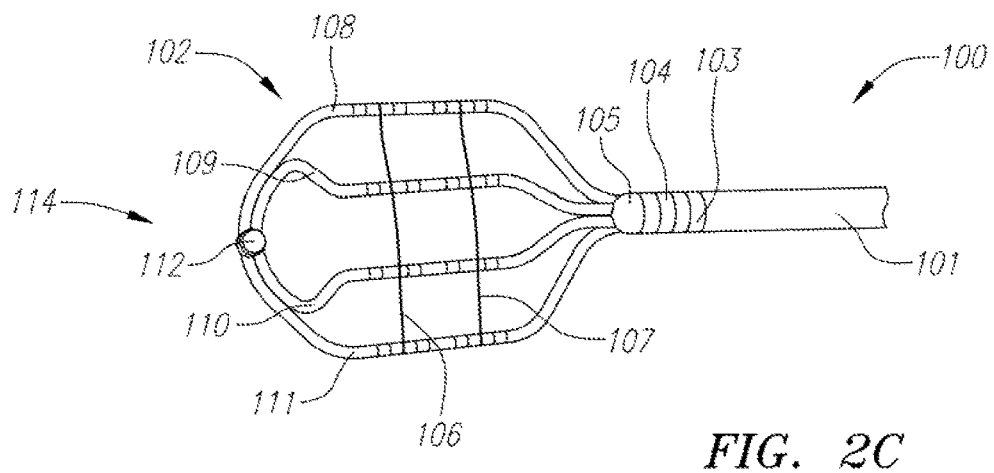
FIG. 2C is an isometric view of another embodiment of a paddle catheter.

FIGS. 2A-2C show embodiments of catheters that can be used for high-density (HD) mapping applications. FIG. 2A illustrates one embodiment of a catheter 10 comprising a catheter body 11 coupled to a paddle 12. The catheter body 11 can further comprise a first body electrode 13 and a second body electrode 14. The paddle 12 can comprise a first spline 16, a second spline 17, a third spline 18, and a fourth spline 19 that are coupled to the catheter body 11 by a proximal coupler 15 and coupled to each other by a distal connector 21 at a distal end of the paddle 22. In one embodiment the first spline 16 and the fourth spline 19 can be one continuous segment and the second spline 17 and the third spline 18 can be another continuous segment. In other embodiments the various splines can be separate segments coupled to each other. The plurality of splines can further comprise a varying number of electrodes 20. The electrodes in the illustrated embodiment can comprise ring electrodes evenly spaced along the splines. In other embodiments the electrodes can be evenly or unevenly spaced and the electrodes can comprise point or other types of electrodes. FIG. 2B illustrates another embodiment of a catheter 30 that can be used for HD mapping applications. The catheter 30 can comprise a catheter body 31 coupled to a paddle 32. The catheter body 31 can further comprise a first body electrode 40 and a second body electrode 41. The paddle 32 can comprise a first spline 34, a second spline 35, a third spline 36, and a fourth spline 37 that are coupled to the catheter body 31 by a proximal coupler 33 and coupled to each other by a distal connector 38 at a distal end of the paddle 39. In one embodiment, the proximal coupler 33 can further comprise an electrode.

Electrode placement along splines is controlled by the good mechanical stability of electrodes on splines. As a result, spacing along splines is best determined not by the mapping system, but by design and manufacturing. But spacing between splines is variable as a result of the forces and torques experienced as a catheter is maneuvered to a desired location. Electrodes located in spline midsections are most vulnerable to displacement. FIG. 2C shows incorporating slender tensile elements configured to join the splines near their centers to limit the maximal displacement from one another. One means to accomplish this is to use slender mono or multifilament nylon thread or suture like material, fastened at the ends, and looping around splines in the middle. A pass through a reflow oven during production allows the threads to become incorporated into the spline's polymer insulation, securing the thread to each spline and minimizing protuberances.

FIG. 2C illustrates one embodiment of a catheter 100 using tethers to limit the maximal spread between splines and thus enforce a more consistent electrode spacing when in use. The catheter 100 can comprise a catheter body 101 coupled to a paddle 102. The catheter body 101 can further comprise a first body electrode 103 and a second body electrode 104. The paddle 102 can comprise a first spline 108, a second spline 109, a third spline 110, and a fourth spline 111 that are coupled to the catheter body 101 by a proximal coupler 105 and coupled to each other by a distal connector 112 at a distal end of the paddle 114. The paddle 102 can further comprise a first support member 106 and a second support member 107 to limit displacement of the splines from each other. These support members can be slender tensile elements (like threads or suture material) that collapse during insertion of the catheter 100 into a sheath. The catheters shown in FIGS. 2A, 2B, and 2C are further described in international application no. PCT/US2014/011,940 filed 16 Jan. 2014 and published in English on 24 Jul. 2014 under international publication no. WO 2014/113612 (the '612 application) and U.S. provisional application No. 61/753,429, filed 16 Jan. 2013 (the '429 application). The '612 application and the '429 applications are both hereby incorporated by reference in their entirety as though fully set forth herein.

Figure 3:
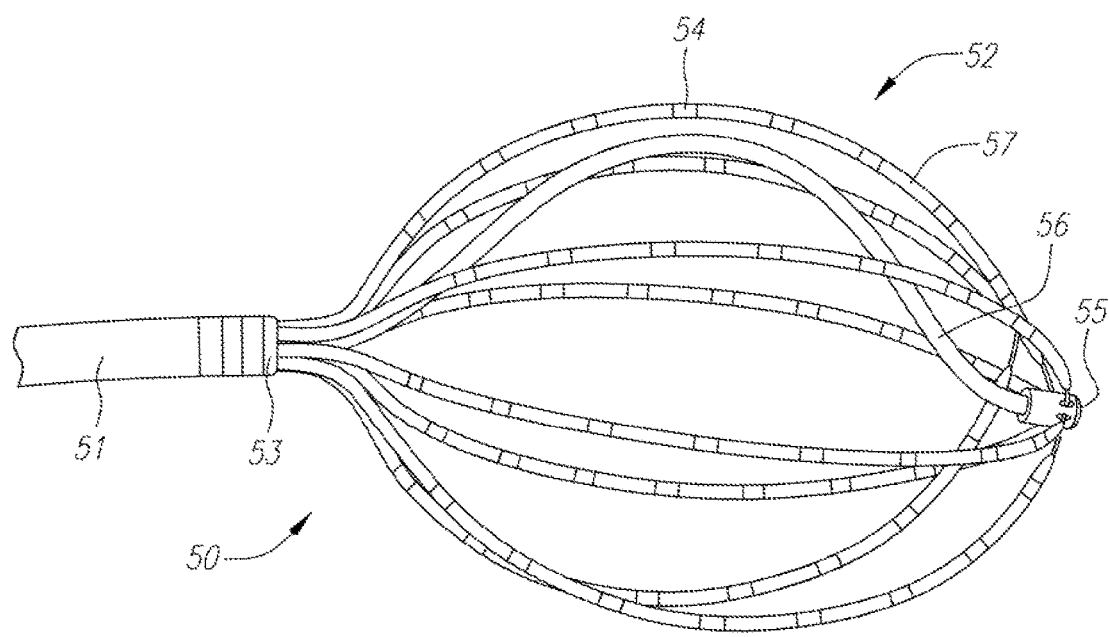
FIG. 3 is an isometric view of a basket catheter.

FIG. 3. Illustrates an embodiment of a basket catheter 50 which can be considered to be a 2D array of electrodes distributed over an ellipsoid surface. The basket catheter 50 can comprise a catheter body 51 coupled to a basket 52. The basket 52 can be coupled to the catheter body with a proximal connector 53. The basket 52 can comprise a plurality of splines 57, a distal coupler 55, and an irrigation tubing 56. Each of the plurality of splines 57 can comprise at least one electrode 54. In the illustrated embodiment, each of the plurality of splines comprises 8 electrodes. The exact number of electrodes can be varied based on the desired characteristics. The basket catheter shown in FIG. 3 is further described in U.S. provisional application No. 61/936,677, filed 6 Feb. 2014, which is hereby incorporated by reference as though fully set forth herein Current techniques to estimate conduction velocity and the direction of activation generally rely on the precise determination of activation times over precise distances. The techniques to assign times to signal locations can result in predictions that are not accurate under certain conditions. The method below utilizes the fundamental concept of wave propagation and does not rely on LAT (local activation time) detection algorithms. This approach is more robust and consistent. Certain extensions are also described that specialize and enhance the application to 2- and 3-dimensional arrangements of electrodes on cardiac surfaces. With each depolarization, the local electric field vector, E, sweeps out a loop like trajectory governed by anatomic and physiologic factors adjacent to these arrangements of electrodes. Two dimensional electrode arrangements allow the resolution of $E_t$, the "tangent bipole vector", which is a useful orientation independent signal to which wave propagation principles can be applied and can be used to introduce a scalar version of $E_t$ along the unit activation direction â, and call it $E_a$. Three dimensional electrode arrangements allow the resolution of a second equivalent bipole component of E along the surface normal direction denoted n̂ called $E_a$. Finally, both 2- and 3-dimensional electrode arrangements allow determination of the E field along the direction $\hat{w}=\hat{n}\times\hat{a}$ called $E_w$ which for a wave traveling in direction $\hat{a}$ is a very small signal.

Figure 4:
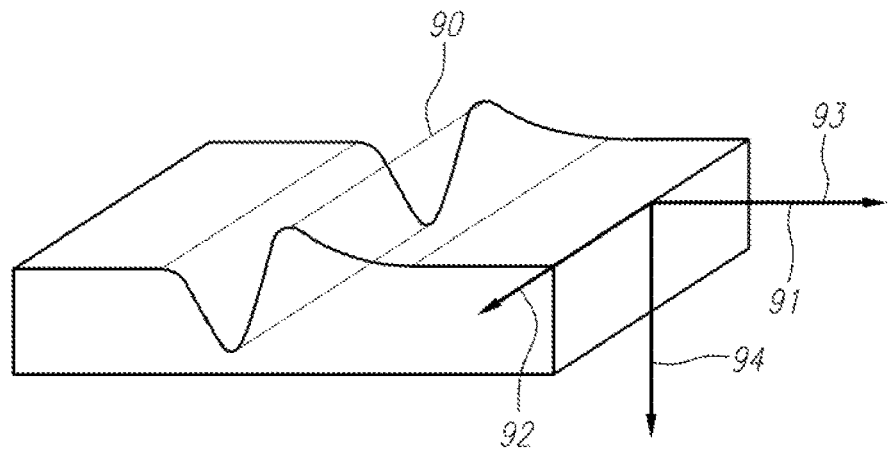
FIG. 4 is an illustration showing the activation, wavecrest, surface normal, and conduction velocity directions for a traveling wave.

FIG. 4 illustrates the unit activation vector 91, wavecrest vector 92, surface normal vector 94, wavefront crest 90, and conduction velocity direction 93. A single depolarization wavefront 90 is depicted based on a unipolar traveling wave voltage signal, $\varphi(x,y,z,t)$. Propagation of the depolarization wavefront 90 occurs from left to right in the view. The depolarization wavefront 90 does not have to conform to a specific shape for the discussion within this disclosure to be valid, but a benefit can be found from physiologic unipolar morphology.

The catheter orientation independent omnipole signals $E_n$ and $E_a$ possess characteristic shapes and amplitudes in normal myocardium. This can be further seen in FIG. 10A. These permit more robust determinations of EP characteristics such as electrogram amplitude, activation timing, and conduction velocity by traditional means.

The next section explains the derivation of the omnipole or "equivalent bipole" signal $E_a$ using a high density catheter such as one of the catheters 10, 30, 50 shown in FIGS. 2-3. The paddle catheter, basket catheter, or other high density catheter is presumably maneuvered such that some or all adjacent electrodes lie flat on the surface/substrate. For convenience the following will use language indicating all catheter electrodes lie on the surface (i.e. the catheter lies on the surface) but the language refers to those electrodes that do lie on the surface or are sufficiently close to be indistinguishable from those that do.

The E-field (E) in the plane of the surface can be calculated using electrode locations X and the potentials measured at the electrodes $\varphi$ using the following equations (where $d\varphi$ and $dX$ have been derived from X, $\varphi$, and subtraction matrix F, as described in international application no. PCT/US2014/037,160 filed 7 May 2014 and published in English on 13 Nov. 2014 under international publication no. WO 2014/182822 (the '822 application) and U.S. provisional application No. 61/855,058, filed 7 May 2013 (the '058 application). The '822 application and the '058 applications are both hereby incorporated by reference in their entirety as though fully set forth herein. The information is also further described in international application no. PCT/US2015/017,576 filed 25 Feb. 2015 (the '576 application) and U.S. provisional application No. 61/944,426, filed 25 Feb. 2014 (the '426 application). The '576 application and the '426 applications are both hereby incorporated by reference in their entirety as though fully set forth herein. The equations have the same form for both 2D and 3D situations:

$$d\varphi = -(dX)^T \cdot E \quad (1)$$

$$E = -((dX)^T)^+ d\varphi \quad (2)$$

where $\varphi$—vector of unipolar potentials,
$d\varphi$—vector of bipolar potentials with respect to a common reference electrode,
X—matrix of mapping system coordinates for the electrodes,
dX—matrix of bipolar displacements with respect to the reference electrode location, and
$A^+$ is the Moore-Penrose generalized inverse of matrix A. However, for the 2D case where electrodes lie almost exactly in a single plane, the resulting E-field can be constrained to that plane. This may be done, for example, by fitting a plane to locations X, and by denoting a unit normal vector to this plane as $\hat{n}$, eliminating any contribution in direction $\hat{n}$ and thus obtaining $E_t = E - (E \cdot \hat{n})\hat{n}$.

Figure 5:
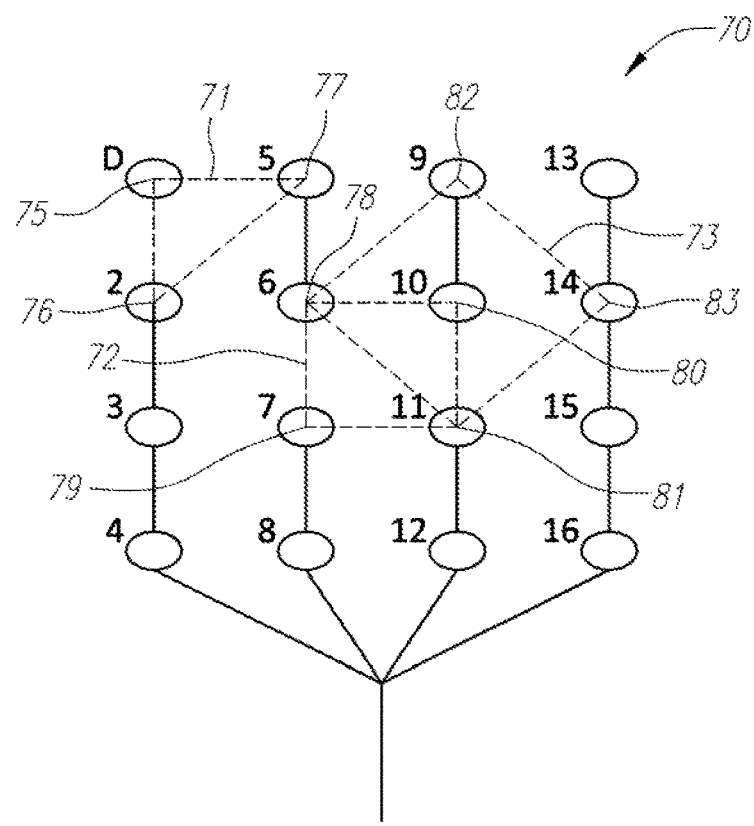
FIG. 5 is a schematic illustrating electrode location and clique geometry.

FIG. 5. Illustrates one embodiment of a paddle catheter 70 showing 16 electrodes and some of the sets of electrodes that can be used to determine $E_t$. In the illustrated embodiment, the paddle catheter 70 can comprise four splines with each spline comprising four electrodes. Any 2D electrode set with at least three adjacent non-collinear electrodes forms a clique and can be used for the calculations. A three electrode clique 71, a four electrode clique 72, and a five electrode clique 73 is illustrated on the paddle catheter 70 in FIG. 5. The three electrode clique 71 can comprise electrodes D 75, two 76, and five 77. The four electrode clique 72 can comprise electrodes six 78, seven 79, ten 80, and eleven 81. The five electrode clique 73 can comprise electrodes six 78, nine 82, ten 80, eleven 81, and fourteen 83. As can be seen by the above illustration, the same electrode on the catheter can be used for multiple cliques.

The local E-field at a position on the surface can be calculated from sets of sufficient nearby electrodes (also referred to as a clique) on the catheter as illustrated in FIG. 5. As indicated generally by dashed lines in FIG. 5, for example, a 2-dimensional clique may comprise a set of three or more electrodes (e.g., electrodes D, 5, 2) located along a plane of the catheter. When only a unipole or bipole is present, the clique can be referred to as a degenerate clique. A degenerate clique is unable to be used to determine orientation independent assessments of directional quantities. A unipole degenerate clique, while orientation independent, has no real directional information. When, for example, more than 3 electrodes are used in a clique, the bipolar signals over-determine the 2D field, e.g. $E_t$. In such an instance, where the clique has more electrodes than strictly necessary for its 2D or 3D role, the clique is overdetermined and admits "subcliques." Subcliques are themselves cliques which may or may not be minimal depending on how overdetermined the original clique was to start with and what subclique is being reviewed. Cliques that are not degenerate allow omnipoles and subcliques allow a unique direct demonstration of orientation independent sensing (OIS) superiority over traditional bipoles. OIS can be uniformly better than bipoles in determining many EP characteristics, including amplitude, timing, conduction velocity direction and magnitude. Although FIG. 5 only illustrates cliques comprising three (electrodes D, 5, 2) 71, four (electrodes 6, 10, 11, 7) 72, and 5 (electrodes 9, 14, 11, 6, 10) 73 neighboring electrodes, the method can be extended to other cliques with more electrodes on the catheter. Since the catheter is assumed to lie flat on the substrate, the full 3D vector E at any clique is also expected to have components in the 2D tangent plane of the endocardial or epicardial surface. As a result, the term $E_t$ is used to describe the component of the E-field in the tangent plane.

One method of determining the local E field is to choose one electrode from the clique as a reference electrode and determine n−1 bipolar potentials (d$\varphi$) and displacements (dX) with respect to the reference electrode. Another method of determining the local E field is to determine all possible distinct bipoles (n*(n−1)/2) from the clique's n electrodes to compute d$\varphi$ and dX. Determining all possible distinct bipoles can lead to a more robust determination of the E-field as it reduces "2nd order" orientation effects that result from the electrode distribution with respect to wavefront.

Let $\hat{a}$ and $\hat{w}$ be unit vectors in the tangent plane along the activation and wavefront directions as illustrated in FIG. 4. For an ideal, homogenous wavefront, $E_t$ is expected to be either parallel or anti-parallel to the activation direction (â) with very little component along the wavefront direction (ŵ). The scalar $E_a$ (also the equivalent bipole or omnipole activation signal) can be defined using the inner or dot product as $$E_a = E \cdot \hat{a} = E_t \cdot \hat{a} \quad (3)$$

$E_a$ is the equivalent bipolar EGM that would be measured on the cardiac surface if one were to place a pair of bipoles separated by 1 mm along the activation direction. By definition, $E_a$ is catheter and clique orientation independent and hence its morphology and amplitude should purely be a function of the local substrate. By virtue of it being a bipolar signal, it is also expected that it would be largely free of far-field artifacts and can possess a stable isoelectric baseline.

The two signals thus resolved ($E_n$ and $E_a$) are significantly independent of each other, opening the possibility of learning more from local EGM signals. The algorithm to determine â from $E_t$ will be explained below.

The conduction velocity can be derived from the E-field using traveling wave concepts. The potential is recognized to be a function of space and time. Propagation of a traveling wave with velocity $v=(v_x, v_y, v_z)$ implies that the wave at time $t_0$ matches exactly the wave at a time $t_0+t$ at coordinates $x+v_x t$, $y+v_y t$, and $z+v_z t$. As a result $$\varphi(x_0, y_0, z_0, t_0) = \varphi(x_0+v_x t, y_0+v_y t, z_0+v_z t, t_0+t) \quad (4)$$

for all initial times and locations $t_0$, $x_0$, $y_0$, $z_0$ and for all times t. Taking the total derivative of both sides of the above equation with respect to time leads to $$0 = \frac{\partial \varphi}{\partial x} v_x + \frac{\partial \varphi}{\partial y} v_y + \frac{\partial \varphi}{\partial z} v_z + \frac{\partial \varphi}{\partial t}$$

which we note is equivalent to $$0 = \nabla \varphi \cdot v + \dot{\varphi} \quad (5)$$

where v is a vector representing cardiac conduction velocity. Recognizing that $E = -\nabla \varphi$ and that only the component of E-field in the tangent plane contributes to the inner product, we get $$E_t \cdot v = \dot{\varphi} \quad (6)$$

$$E_a(\hat{a} \cdot v) = \dot{\varphi} \quad (7)$$

The conduction velocity vector v can then expressed as $$v = \frac{\dot{\varphi}}{E_a} \hat{a} \quad (8)$$

The magnitude of conduction velocity, a presumed constant during local depolarization, is recognized to be the ratio of the time derivative to the spatial derivative along the direction of activation in the tangent plane of the potential. It is then expected that under ideal conditions, the morphology of $E_a$ would be similar to that of $\dot{\varphi}$ with the only difference being a scale factor which would be the velocity magnitude. The activation direction (â) can be determined to be the direction in the tangent plane that results in the maximum correlation between $\dot{\varphi}(t)$ and $E_a(t)$. Although the expression (8) above holds in principle at every time point during local depolarization and location within the clique, when signal levels are sufficiently small or isoelectric, the ratio of $\dot{\varphi}$ to $E_a$ cannot be meaningfully determined.

The analysis can be expected to be more robust when the electrodes that form a clique are in good contact with the surface. This can be checked and enforced a priori using some or all of the criteria below. The criteria to check whether a clique is in good contact with the surface can be applied together or separately as determined by the user or process. Automatic application of the first six criteria can form an important component of the disclosure as getting uniform contact of all electrodes is generally difficult for any catheter, particularly so for small basket catheters.

The first criteria looks at the angular deviation between a 3D mapping systems determined surface normal near the clique and the normal to the plane that best fits the electrodes on the clique and determines whether they are below a threshold. The second criteria looks at the angular deviation between the normal corresponding to the clique of interest and the normal corresponding to the neighboring cliques and determines whether they are below a threshold. The third criteria looks at the distance between the electrode locations that form the clique and the surface and determines whether they are below a threshold. In one embodiment, the second criteria further includes ensuring that the local curvature is not above a threshold. The fourth criteria looks at the amplitudes of the unipolar signals obtained from the electrodes on the clique and determines whether they exceed the noise level and are within a typical range. The fifth criteria looks at the morphologies of the unipolar signals obtained from the electrodes on the clique and determines whether they are typical (e.g. modest upstroke followed by a dominant down deflection and fairly prompt return) and reasonably consistent. In another embodiment, an additional criteria can be used by looking at the morphologies of $\dot{\varphi}$ to determine whether they are typical and reasonably consistent. Unipolar signals $\varphi(t)$ can also sufficiently resemble omnipole signal $-E_a(t)$. The sixth criteria looks at the amplitudes, shapes, and morphologies of $E_t$, and $E_a$ obtained from the clique and determines whether they are typical. Omnipole signal $E_a(t)$ can sufficiently resemble $\dot{\varphi}(t)$. The seventh criteria looks at the visual cues for good contact such as fluoro, ICE, etc. as well as tactile sensations and maneuvering history on the part of a catheter operator. While seven criteria are listed herein to check whether a clique is in good contact with the surface, not all seven of the criteria listed have to be used to make that determination. Further, other criteria can also be used to determine whether a clique has made good contact with a surface.

Conduction velocity once derived can be displayed with a 3D mapping system on the chamber geometry using, for example, arrows, with the direction of the arrow indicating the activation direction and the color, length, or width of the arrow showing the magnitude. In another embodiment an interpolated color map can also be used to display conduction velocity magnitude with or without arrows of uniform length showing the direction. In another embodiment, conduction velocity vector maps can also be coupled with voltage amplitude or LAT maps. Generally, the display is updated immediately following each local depolarization and persisting or gradually fading out until the next local depolarization. Finally, some or all isochrones may be displayed as curved lines on the cardiac surface, for instance at specific intervals since the start of depolarization such as 0, 10, 20, and 30 ms. This reduces visual clutter and allows a more interpretable superposition of conduction velocity arrows. In another embodiment, some or all isochrones may be displayed as curved lines on the cardiac surface, for instance at specific intervals since the start of depolarization such as 0, 20, 40, and 60 ms.

As can be readily appreciated from equations 1 and 2 listed above, it is important to have reasonably accurate electrode displacements (dX) and electrode positions (X) to judge contact and the local surface tangent plane so as to portray the signals and resulting EP characteristics including conduction velocity accurately. It has been suggested that impedance based mapping system locations are more robustly determined from tip or circumferential ring electrodes than from small surface area electrodes on portions of a catheter shaft. Nevertheless, the issue can remain significant in catheter designs with small ring electrodes on flexible splines. Small electrodes, owing to their high electrode-electrolyte impedance can be difficult to locate accurately—they are more susceptible to artifact and can be biased toward the system reference "belly patch" electrode. Compensation algorithms can be used to correct for the positions. However, they rely on a priori knowledge of the construction and inter-electrode distances. Flexible splines can deform, bunch up, or become separated (splayed) in vivo under certain conditions resulting in important deviations from their nominal design. When that happens, the compensation algorithms referred to above may not be able to effectively correct electrode location errors. Means to prevent the deformations, bunching, and separation of catheter splines and electrodes from becoming severe enough to significantly disturb assessments of EP characteristics are also disclosed above in relation to FIG. 2C.

Figure 6:
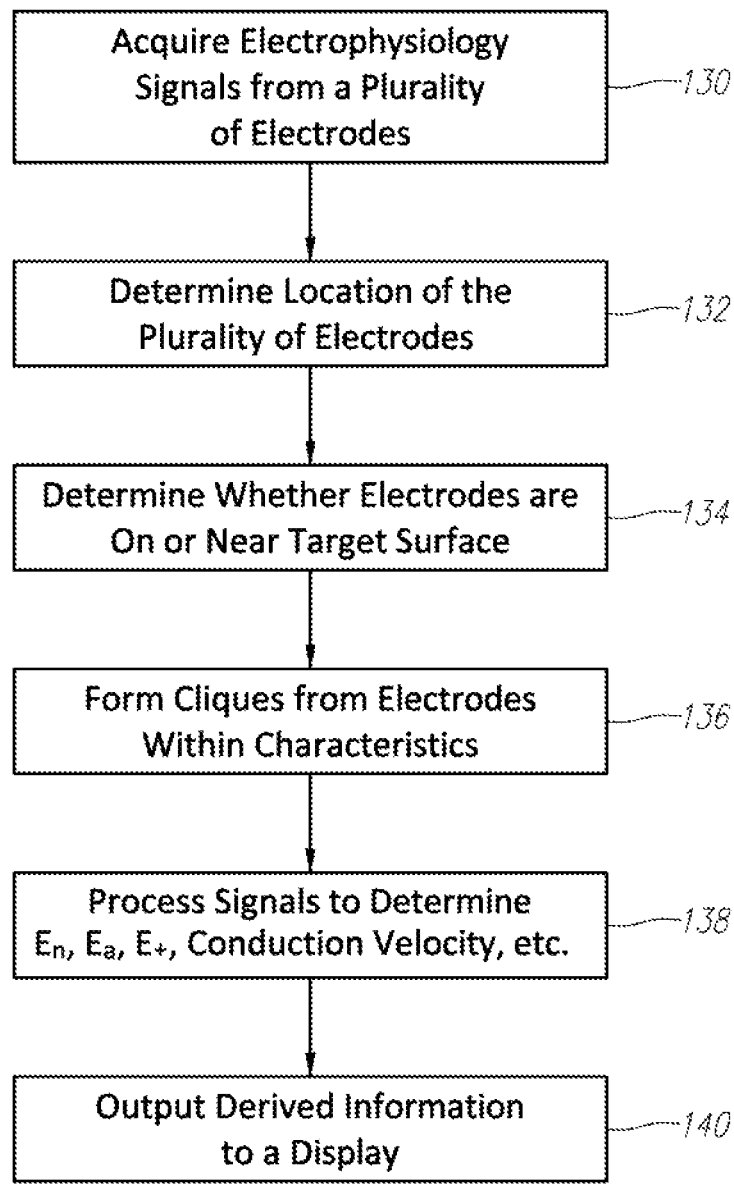
FIG. 6 is a flow chart showing a step-by-step approach to acquire, determine, and output orientation independent information.

FIG. 6 illustrates a flowchart showing a step-by-step approach to acquire, determine, and output orientation independent information. The method illustrated in the flowchart can comprise the following steps:

At step 130 acquire electrophysiology signals from a plurality of electrodes.

At step 132 determine the location of the plurality of electrodes in step 130.

At step 134 determine whether the plurality of electrodes are on or near the target surface.

At step 136 form cliques from the electrodes that fit within defined characteristics for inclusion in cliques.

At step 138 process the electrophysiology signals to determine $E_n$, $E_a$, $E_t$, conduction velocity, and other orientation independent characteristics such as amplitude or timing.

At step 140 output the derived information to a display.

Helical basket catheters have been proposed as a means to achieve more uniform coverage of electrodes over the extent of a basket. This can be a desirable characteristic for this disclosure on its own, but also for the increased stiffness (and thus resistance to displacement) that results. Increased stiffness can allow for reliance on the spacing as determined by design and manufacturing rather than the mapping system location for each electrode.

Figure 7:
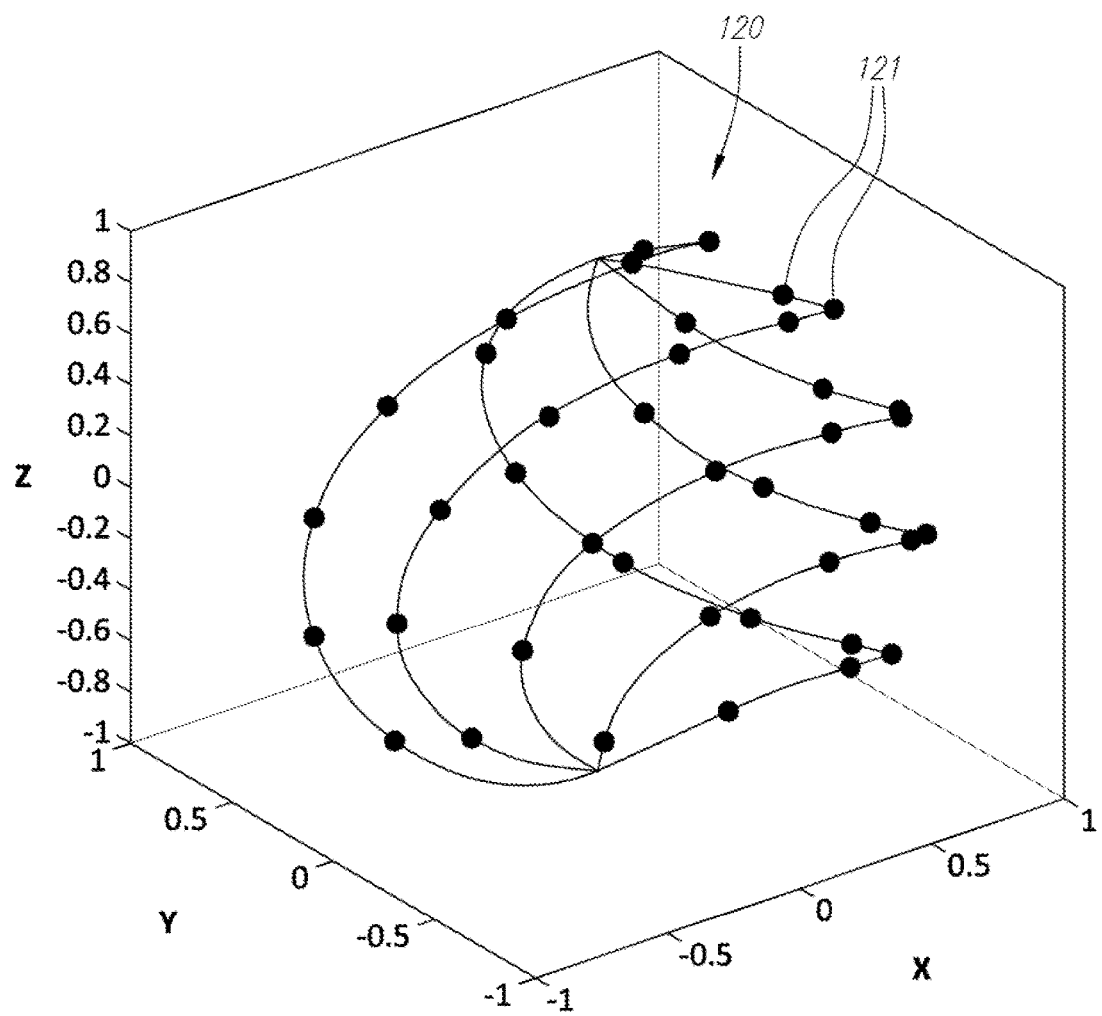
FIG. 7 is a diagrammatic view of helical basket catheter design with non-uniform electrode spacing along splines but uniform spacing over the ellipsoidal basket surface.

FIG. 7 illustrates a helical catheter design of a catheter 120 with non-uniform electrode spacing along splines but achieves a nearly uniform electrode dispersal over the outer surface of the basket. Each point 121 in the figure represents an electrode. The catheter illustrated in FIG. 7 is further described in U.S. application Ser. No. 13/790,110, filed 8 Mar. 2014, (the '110 application) which is hereby incorporated by reference as though fully set forth herein.

Beam buckling theory suggests compliance goes as the length dimension squared so half the length translates to 4 times stiffer. With small size, then, come the benefits of: (a) interelectrode spacing more consistent under varying use conditions, (b) more dense sampling and thus better spatial resolution, and (c) the capacity to be maneuvered into full contact positions and orientations.

As discussed earlier, conventional mapping techniques suffer from bipole orientation induced amplitude and morphology uncertainty which also adversely affects activation timing. Challenging arrhythmias in clinical EP today may involve features such as channels with low amplitudes and slow conduction that are only of the order of 5 mm in width. Detailed maps are often not required over an entire cardiac chamber but confined to certain locations where pathology often appears or other diagnostic tests such as surface ECGs, ultrasound, MRI, or even basic EP catheter signals indicate. What is important is that the information reliably reflect the state of the myocardium locally and that it do so with adequate resolution.

The algorithm discussed in the invention can be used to derive local E-fields (including E and $E_t$), and equivalent bipolar signals ($E_n$ and $E_a$) with orientation independent amplitudes and reliable morphology/timing, and instantaneous conduction velocity vectors. Such characterization can permit improved maps of substrate amplitude (using $E_n$, $E_a$, or measures of E or $E_t$ loop size such as maximal dimension also known as $E_{span}$), activation times (LAT), conduction velocity (magnitude and direction), as well as an index of inhomogeneous conduction derived from $E_w$ or the eccentricity of $E_t$. Bipolar-like omnipole signals of consistent morphology may be understood from the fundamentals of cell depolarization and unipolar EGM signals when in proximity to active tissue.

One or more of these characteristics can also enable clinicians to perform more reliable scar border delineation (known to contribute to VT and other arrhythmias). Also, local determinations of low amplitude and/or slow conduction velocity can help identify critical pathways such as isthmuses for arrhythmias that are amenable to ablation therapy. More reliable EGM amplitudes and morphologies can also allow better measures of EGM reduction measures, lesion characterization, or the local assessment of conduction velocity as a critical isthmus is affected or a lesion gap approached.

OIS technology can also be utilized with implanted medical devices. Implanted medical devices responsible for rhythm discrimination currently rely primarily on depolarization event timing. Timing alone however can fail to distinguish between important rhythms as the times of occurrence can be similar, and multi-chamber algorithms are not sufficiently specific. The application of OIS to an implanted device's catheter or lead can establish a baseline direction and speed (using OIS characterizations) for healthy rhythms.

Implanted devices already perform elementary mapping system functions, but with OIS technology as discussed herein, can better track the number and degree of abnormality of beats and can group them by similarity in detection criteria. For example, a non-physiologic heart rate increase typically would cause the conduction velocity to decrease, while a physiologic cause for heart rate increase, like exercise, would not result in a decrease in conduction velocity. Hence the decision to treat this tachycardia can be based not only on changes in heart rate and other traditional ICD metrics such as timing but based on noting the conduction velocity vector's direction and magnitude are consistent with a VT. Some of the detection criteria that can be used by the implanted device can include combinations of rate, number consecutive abnormal beats, frequency "x of y beats", etc.

Observations from one or more sites on implanted leads can also be used to track rate or ischemia induced functional block occurrences with greater accuracy than inferences drawn from timing changes. This in turn can enable patient or health care provider alerts to potential problems with brady or tachy arrhythmias before deciding on treatments with pacing or cardioversion shocks.

Figure 8:
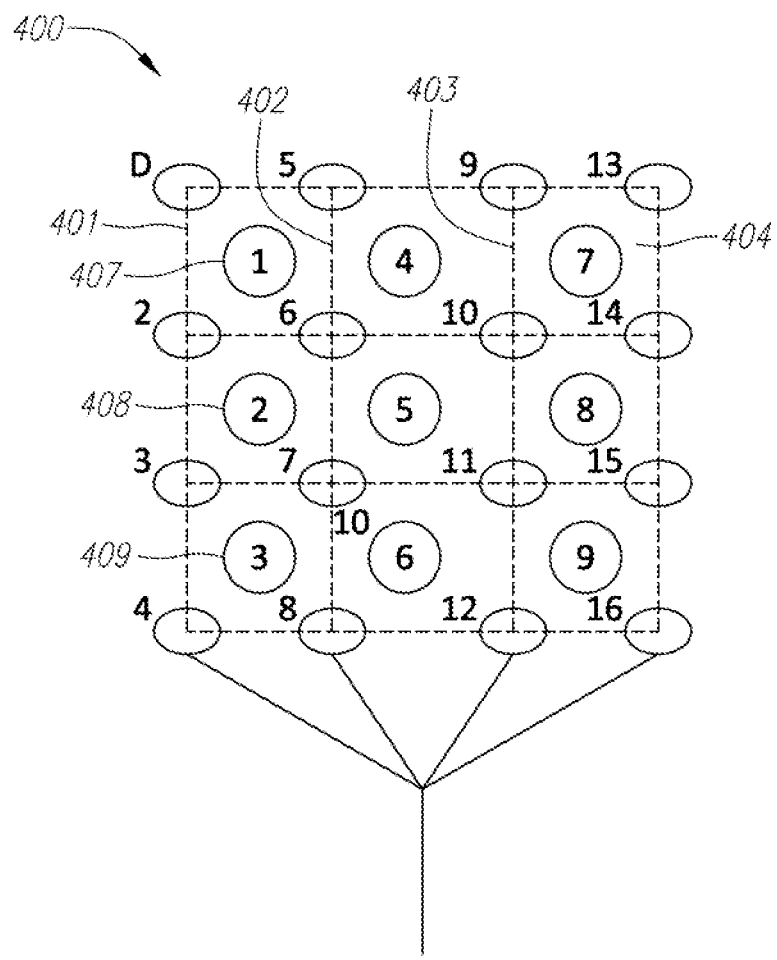
FIG. 8 is a diagram of a paddle catheter and the electrodes and rectangular cliques present on the paddle catheter.

FIG. 8 illustrates a paddle catheter 400 and the cliques used for the computations discussed herein. The paddle catheter 400 can comprise a first spline 401, a second spline 402, a third spline 403, and a fourth spline 404. Each of the splines can comprise four electrodes. For the purpose of validation, cliques comprising four electrodes (two from each pair of adjacent splines as seen in FIG. 8 can be used. In some instances some of the rectangular cliques can be considered to not be in contact with the cardiac surface.

The determination of whether a clique can be considered to be in contact with the cardiac surface can be accomplished in a variety of ways. There are a variety of methods that can be used to determine whether a high quality OIS signal is present.

In one method, the peak-to-peak amplitude ratio of $E_w/E_{span}$ can be used. A low ratio of the peak-to-peak amplitudes of $E_w/E_{span}$ can lead to a finding of a high quality OIS signal. $E_w$ is the signal that remains when $E_n$ and $E_a$ are accounted for and, for an ideal homogeneous wavefront traveling linearly with ideal OIS coordinates should be zero. $E_{span}$ is a term to describe what is the peak-to-peak equivalent amplitude for the entire E field loop. $E_{span}$ is the maximum over all of the depolarization's E field point pairs of $|E_i - E_j|$ at time points i and j. Importantly, it does not require ideal wavefronts or coordinates and will be greater than or equal to $E_a$ peak-to-peak and $E_n$ peak-to-peak.

In another method, the cross correlation lags between $E_a$ and $\dot{\varphi}$ can be used. A low cross correlation lag between $E_a$ and $\dot{\varphi}$ can lead to a finding of a high quality OIS signal. In one embodiment, a low cross correlation lag can be defined as typically less than 5 ms for a catheter designs with 1-4 mm between electrodes. In other embodiments, a different value can be used to define a low cross correlation lag. In another method, the conduction velocity can be used to determine the OIS signal quality. A physiologically plausible conduction velocity determination can be used to determine the signal quality at a given location. In one embodiment, a conduction velocity of healthy tissue can be set in the range of 0.4-1.4 mm/ms and the conduction velocity in or near scar tissue can be set in the range of 0.05-1.0 mm/ms. In yet other embodiments other velocities can be used by the system to determine the quality of any OIS signals. A user of the system can further set a different value for the system to use to determine a signal quality.

In yet another method, the amplitude of a unipolar signal can be used. In on embodiment, a unipolar signal amplitude can be determined to be adequate to give a quality OIS signal can be set as 0.5-15.0 mV in healthy tissue. In another method, the unipolar morphology can be used to determine the quality of an OIS signal. A plausible unipolar morphology can be determined by looking for a unipolar morphology that comprises a main portion that either contains a small to moderate sized upward deflection followed by a moderate to large downward deflection or a unipolar morphology that comprises a moderate to large downward one. In another method, the cross correlation between clique unipoles can be used. A good maximal cross correlation between clique unipoles can suggest that the clique unipoles reflect a locally homogeneous assessment of conduction.

In yet another method, a unipolar temporal dispersion over the clique can be used to determine a high quality OIS signal. A unipolar temporal dispersion over the clique, in the range of 1-6 ms for a catheter design with 1-4 mm between electrodes can show a high quality OIS signal. The unipolar temporal dispersion may be determined by conventional dV/dt threshold crossing techniques or by maximal cross correlations. In another method, the derived OIS omnipole signals can be compared to idealized $E_n$ and $E_a$ signals. The closer the OIS signal is to the idealized values, the better the OIS signal. A comparative value can be set within the system or can be set by a user to state the amount of resemblance desired to determine whether a high quality OIS signal is present. In another method, the loop-derived n̂ can be compared to the surface normal from an electroanatomical mapping system. In one embodiment, a good match between a NavX mapping system determined n̂ direction and a loop derived n̂ direction can show a high quality OIS signal. The NavX mapping system can determine an n̂ direction from surface shape and catheter clique electrode locations. In yet another embodiment, electrogram signals with isoelectric intervals can be used to determine whether a high quality OIS signal is present. An isoelectric interval with no baseline drift and no large offset over an OIS analysis interval can be used to determine a high quality OIS signal. In one embodiment the OIS analysis interval can comprise 20-80 ms. In other embodiments, the OIS analysis interval can be longer or shorter or of an interval chosen by a user of the system.

There are also a variety of methods that can be used to determine whether a poor quality OIS signal is present. In one method, the magnitude of the conduction velocity can be used to determine whether a poor quality OIS signal is present. If the conduction velocity magnitudes are larger than would otherwise be expected the system or user can determine that poor quality OIS signals are present. Abnormally large conduction velocity magnitudes can be caused by far field signals since these can often produce very small peak-to-peak $E_a$ values. In one embodiment, if the conduction velocity magnitude is greater than 2-3 mm/ms a poor quality OIS signal can be determined. In other embodiments other values for excessively large conduction velocity magnitudes can be used. In another method, a unipolar EGM signal can be analyzed to determine whether a poor quality OIS signal is present. A unipolar EGM signal that shows a prominent positive deflection persisting for 60-80 or more ms following depolarization can indicate an injury current component to the unipolar EGM signals. In another method, a saturation of one or more EGM channels can reflect pacing polarization and amplifier recovery. This can also lead to a finding of a poor quality OIS signal.

In yet another embodiment, several different methods can be used to determine whether far field artifact could be causing low quality indices. The methods to determine whether far field artifact is causing low quality indices could include one or more of: "beats" where the tentative detections on all unipolar clique electrodes are virtually simultaneous; if the timing of $E_n$ and/or $E_a$ in the atria is sufficiently close to that of the surface QRS and thus suggests a probable ventricular unipolar artifact; and at least one small E-field loop. A small E-field loop can be caused by far field signals that result in E-field loops with very small $E_{span}$. In one embodiment, when the $E_{span}$ value is less than 0.5 mV/mm the system or user can determine that far field artifact is causing low quality indices.

Figure 9:
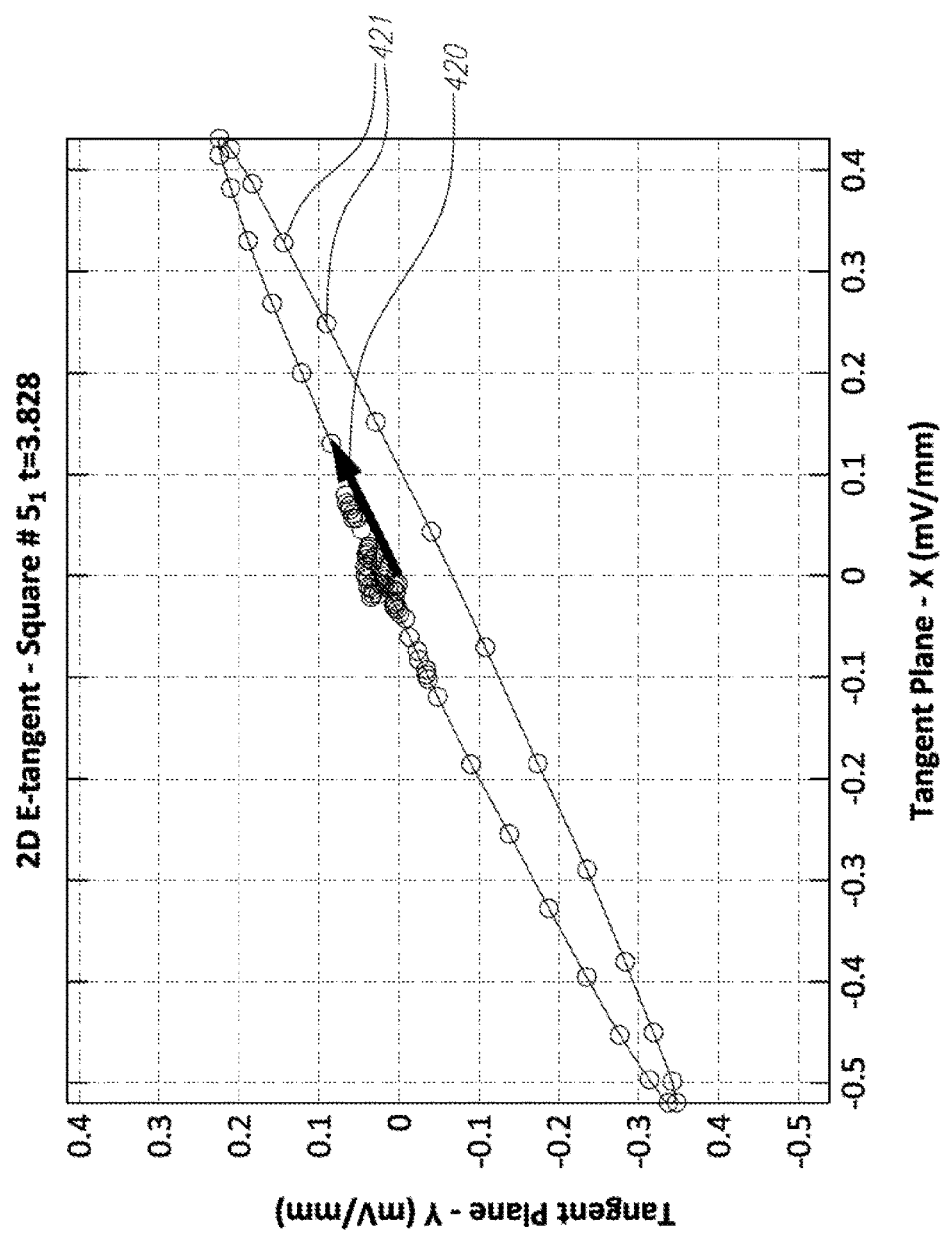
FIG. 9 is a graph of the trajectory of vector $E_t$ over a single beat.

FIG. 9 shows the loop trajectory of vector $E_t$ 420 in the tangent plane over 100 ms of the cardiac cycle when the catheter clique electrodes see atrial depolarization action. If the wavefront passes the clique electrodes progressing uniformly in a homogeneous medium (as seen in FIG. 4), then vector $E_t$ 420 should comprise voltage swings along a dominant axis aligned with the activation direction. The activation direction, calculated using the method described in the previous section is shown using the arrow. The plot shows the trajectory of vector $E_t$ 420 over a single beat. The tail of the vector is anchored at the isoelectric origin and the plurality of dots 421 indicate the path of the head of the E field vector. The vector sweeps a loop around the origin with maximum and minimum excursions along the activation direction (indicated with the arrow).

Figures 10A, 10B:
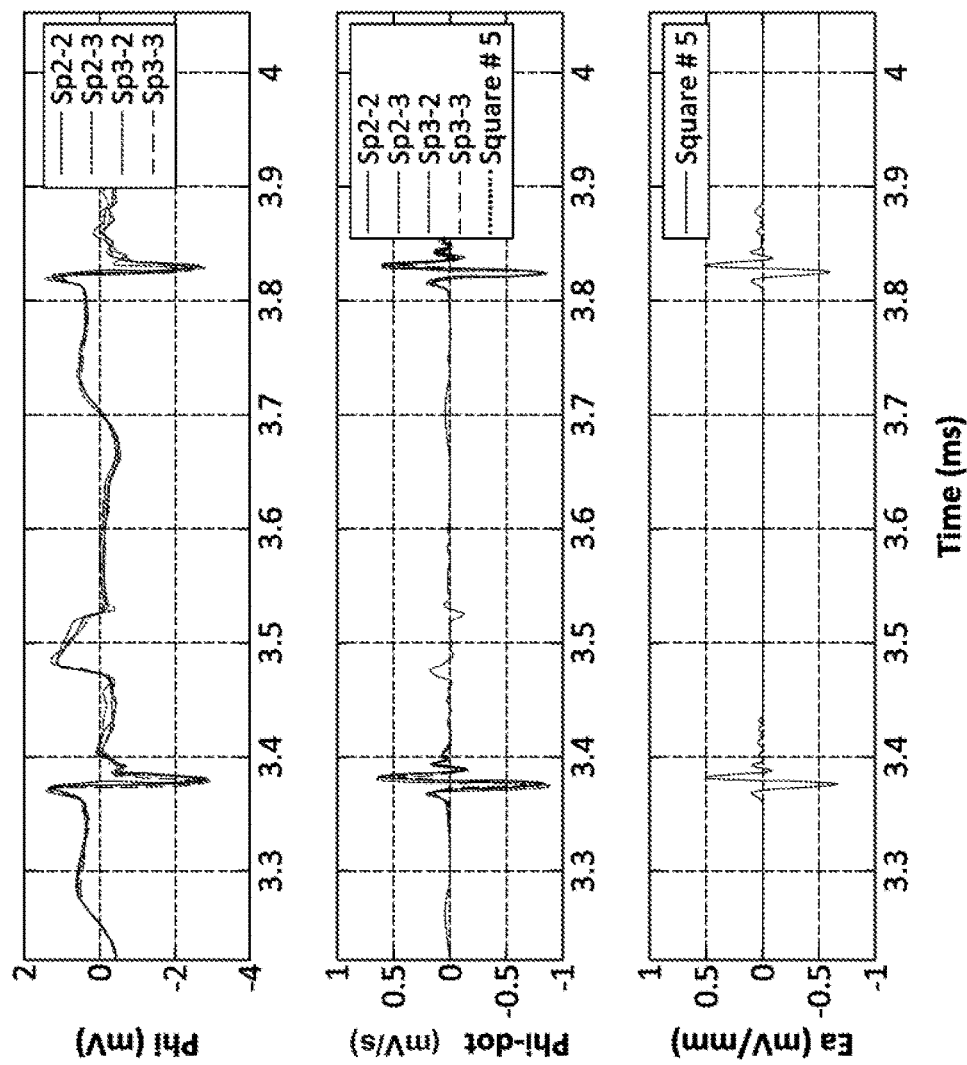
FIG. 10A is a graph showing the EGM signals and equivalent bipole or omnipole $E_a$ vs. time.
FIG. 10B is a line drawing of a shape of an exemplary $E_a$.

FIG. 10A shows the EGM's, their time derivative $\dot\varphi$ (phi-dot) and the "equivalent bipole" $E_a$ plotted as a function of time for two beats. Note that the morphology and amplitude of the signal is consistent from one beat to the other and that the far-field ventricular signal that we see in the unipolar EGM's is largely absent. The exemplary $E_a$ has a negative deflection followed by a prominent sharp positive deflection. Also, its amplitude is expected to be solely a function of the substrate that is being investigated (and not catheter or bipole orientation). FIG. 10B shows the stylized shape of an exemplary $E_a$ with a negative deflection followed by a sharp positive deflection.

Due to various factors that contribute to non-ideal conditions, including finite spatial separation of electrodes, the morphologies of $\dot\varphi$ and $E_a$ do not match exactly but they are very close to proportional. As a result the ratio (velocity magnitude in ideal conditions) is not uniform over the time interval of the beat. Also, when one or both of $\dot\varphi$ and $E_a$ of Equation 8 approaches zero, the algorithm fails to produce meaningful results. Under ideal conditions, $\dot\varphi$ and $E_a$ would tend to zero at the same instant in time and in the limit when they both tend to zero the ratio could be meaningfully evaluated to be the conduction velocity magnitude. In practice zero crossings of the denominator and numerator play havoc with this ratio.

The practical limitations can be overcome by realizing that a classic unipolar signal recorded at an electrode includes contributions from depolarizing tissue upstream and downstream of the electrode location. The information about depolarizing tissue immediately under the electrode is contained within the region of maximal −dv/dt, peak negative deflection, and the immediate up stroke following the unipolar peak negative. This corresponds to the region contained within the peak negative and the subsequent positive peak in $\dot\varphi$ and $E_a$. This region can be seen as time interval 481 in FIG. 11. Conduction velocity is calculated using information from the signals within this region.

Listed below are some practical ways to calculate the velocity of activation or propagation. One way is to calculate the velocity as the ratio of the peak-to-peak values of $\dot\varphi$ and $E_a$. The conduction velocity estimations shown in this section have been evaluated using this method. An equivalent mathematical way to represent a ratio of peak-to-peak values is shown with definite integrals below.

$$v = \frac{\int_{t_b}^{t'_b} \frac{d\varphi}{dt} dt'}{\int_{t_b}^{t'_b} \frac{dE_a}{dt} dt'} \quad (12)$$

In another embodiment the conduction velocity can be calculated by applying different weights to the information contained within the interval ($t_a < t' < t_b$) as follows $$v = \frac{\int_{t_a}^{t_b} w \frac{d\varphi}{dt} dt'}{\int_{t_a}^{t_b} w \frac{dE_a}{dt} dt'} \quad (13)$$

where w(t) is a weighting function. The weighting function can be used to ensure that more importance is given to certain regions within the time interval as shown in FIG. 12 and discussed below.

Figure 11:
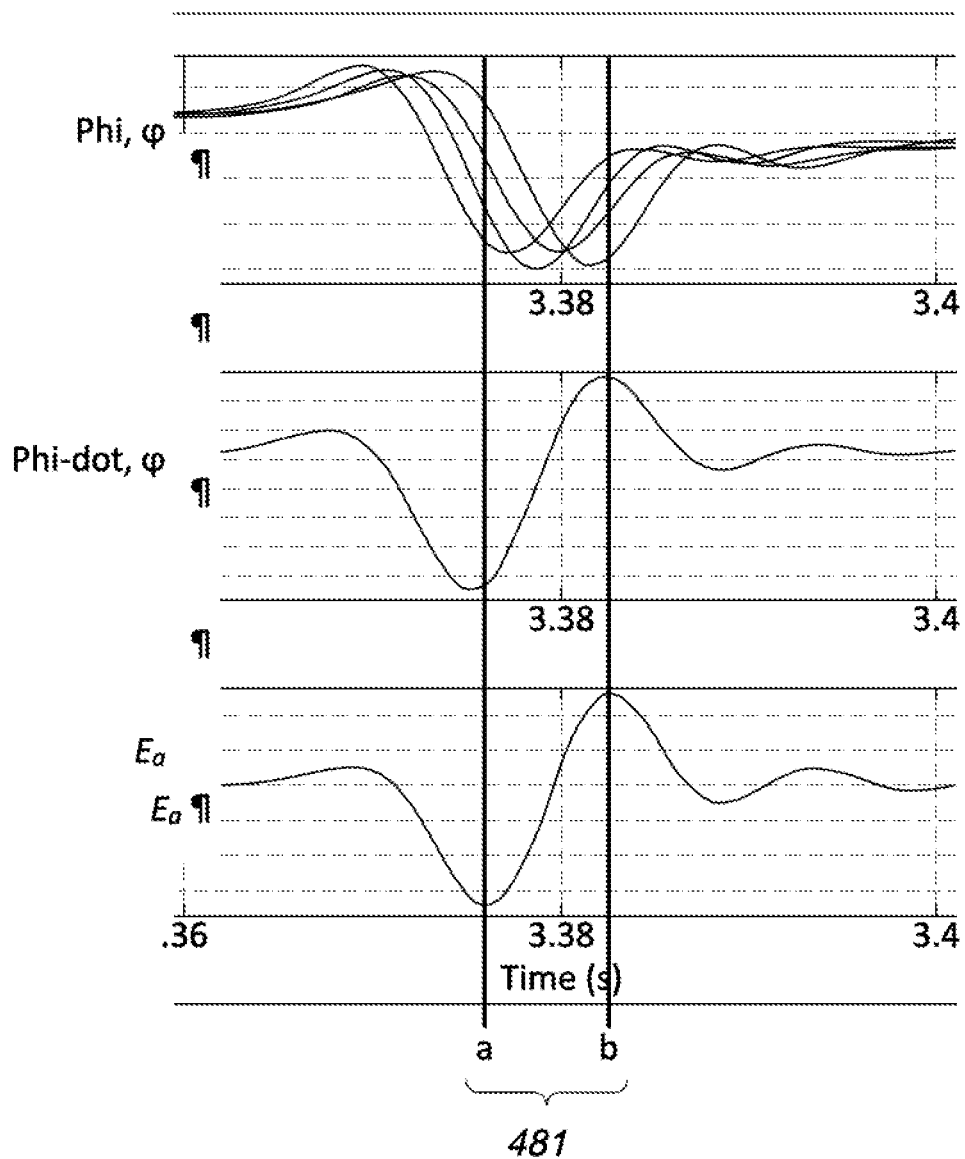
FIG. 11 is a graph showing the time interval that holds the most information about depolarizing tissue under a particular clique of electrodes.

FIG. 11 illustrates a plot showing the time interval (from a to b) 481 that holds the most information about depolarizing tissue under a particular clique of electrodes. This generally corresponds to times around when the unipolar voltage is most negative which is when the inward current of depolarization is maximum under the electrodes of the clique. This introduces a practical and improved means to derive velocity from local $\dot\varphi$ and $E_a$ signals.

Figure 12:
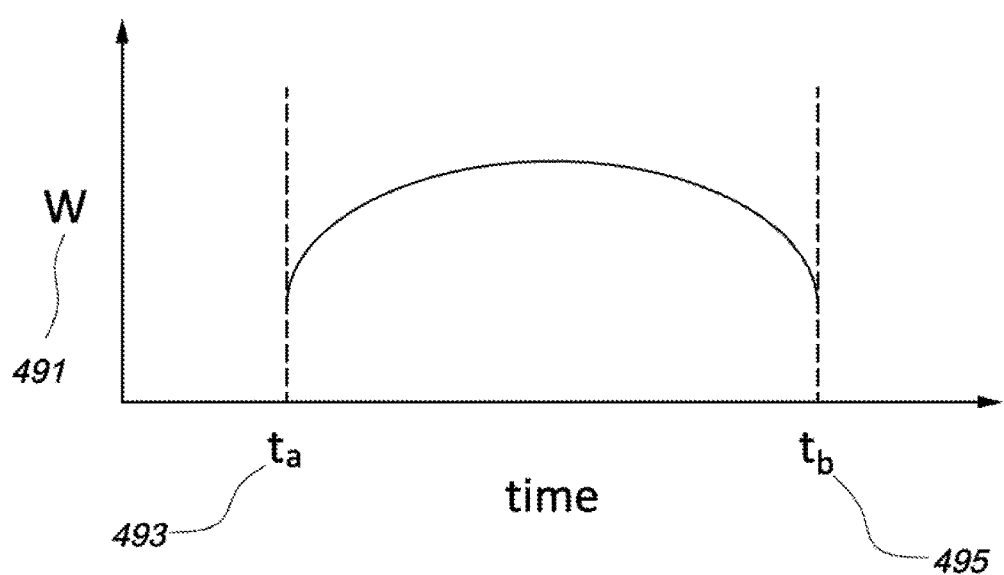
FIG. 12 is a plot showing the weighting function vs. time.

FIG. 12 depicts a weighting function w vs. time. W 491 is shown between time $t_a$ 493 and time $t_b$ 495. In this illustration w is chosen to ensure more importance is given to the region corresponding to the zero-crossing of $E_a$ following its pk-neg.

Figure 13:
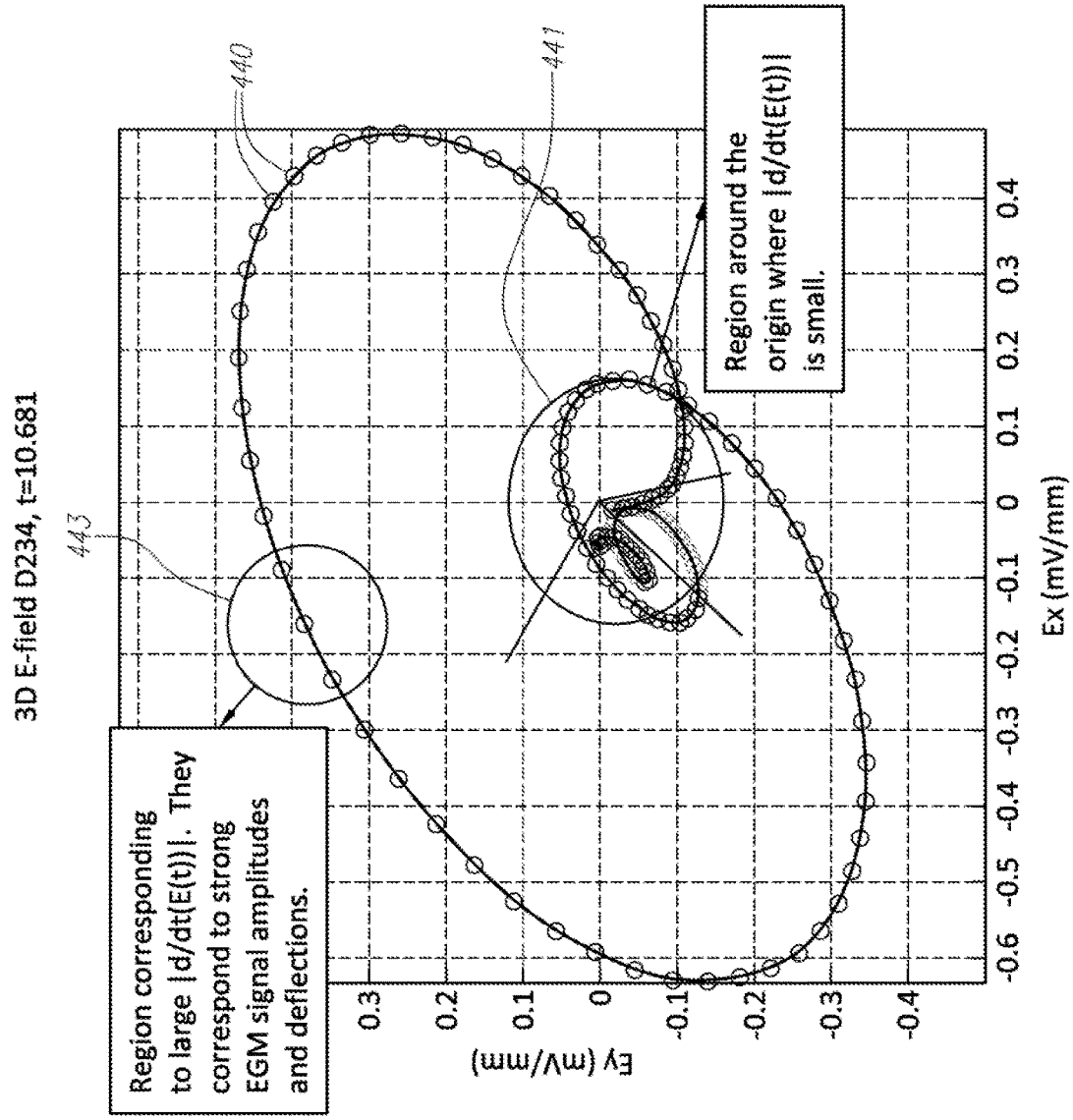
FIG. 13 is a graph of an E-field loop showing regions of large and small $|d/dt(E(t))|$.

In some embodiments, determining the activation direction from the E field loop data can be overly sensitive to data taken when the loop is small and nearly isoelectric. OIS signals and derived quantities may reflect artifacts due to filtering, offsets, far field effects, or waveform complexity when good information also exists. The artifacts can be minimized by weighting the loop points in calculations, including activation direction cross correlation, not equally by time, but proportional to, or as a monotonic function of, |E(t)| or |d/dt(E(t))| as seen in FIG. 13. This can ensure that the E field data points that lie close to the origin or are changing slower than the depolarization, as seen in FIG. 13, are given less weight. Only the major deflections, which provide the necessary and key information about the underlying substrate, are then used for deriving OIS quantities, including the OIS coordinate frame ($\hat{n},\hat{a},\hat{w}$) and omnipole signals $E_n$ and $E_a$. This can concentrate OIS results on the information containing part of the loop when the E field changes rapidly. This weighting can further be used in deriving OIS coordinate directions entirely from the E field loop, which could also lead to more accurate determination of $E_n$ peak-to-peak, $E_a$ peak-to-peak, and conduction velocity magnitude. In another embodiment, when d/dt(Et) is determined to be too high, this can be due to artifacts and can be used in addition to the set of OIS quality criteria discussed above.

FIG. 13 illustrates an E-field loop showing regions of large and small |d/dt(E(t))|. The points 440 are EGM derived E-field points equally spaced in time. As discussed above, closely spaced points contain little information and contain artifacts that can affect OIS derived signals and EP characteristics. The area around the origin 441 has a small |d/dt(E(t))|, while the area with a large |d/dt(E(t))| 443 corresponds to strong EGM signal amplitudes and deflections. The area with a large |d/dt(E(t))| is of more interest. As a result, in one embodiment, those areas with a small |d/dt(E(t))| can be removed or deemphasized.

Figure 14B:
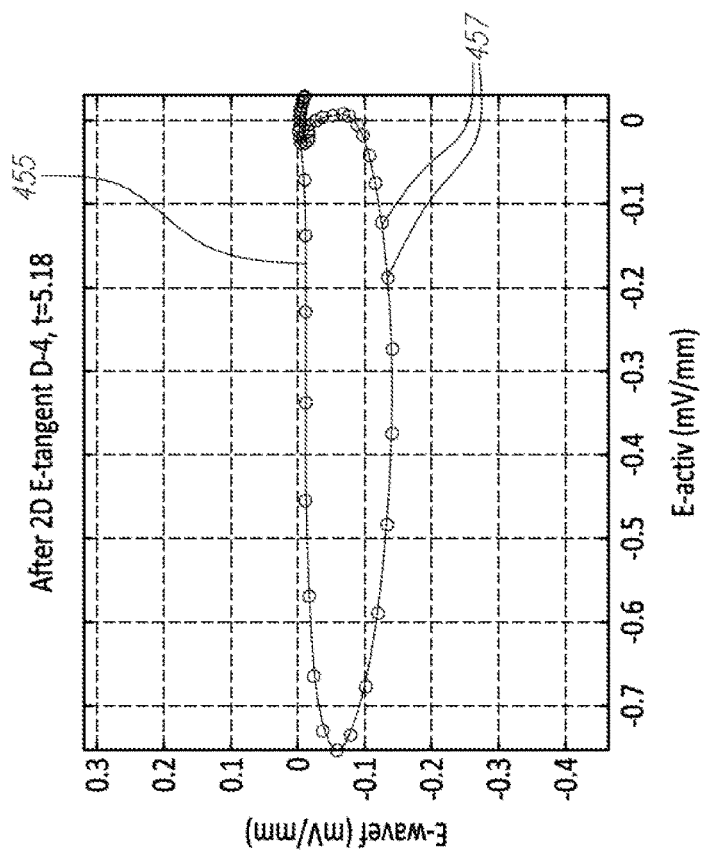
FIGS. 14A and 14B are graphs showing the tangent E-field loop before and after weighting the loop points based on the norm of the E-field.
Figure 14A:
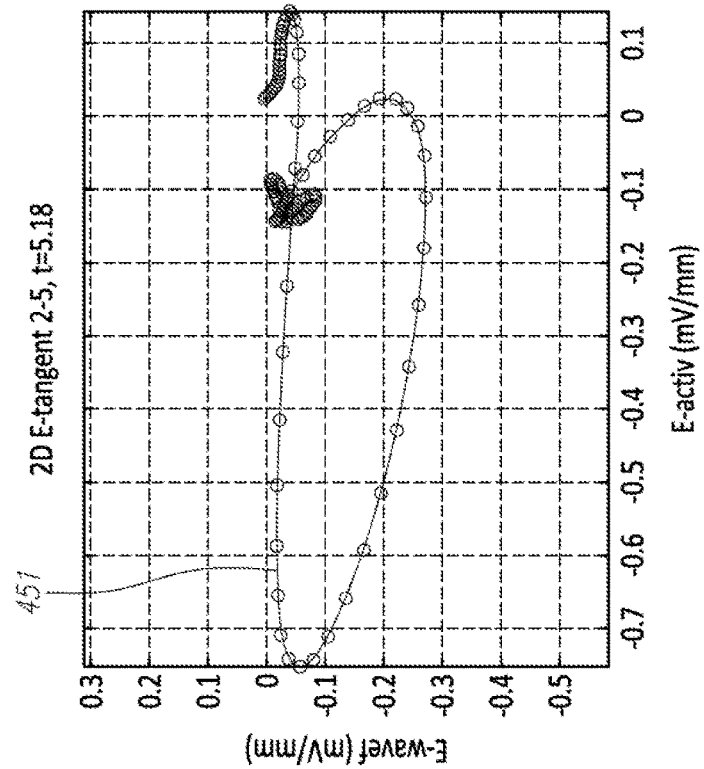

In another embodiment, the loop points can also be weighted based on the magnitude of the E-field (norm(E) or |E|) which is the distance from the isoelectric origin. FIGS. 14A and 14B show the tangent E-field loop points before and after weighting based on the method described herein. FIG. 14A illustrates the tangent E-field loop 451 before weighting. FIG. 14B illustrates the tangent E-field loop 455 after weighting the loop points 457 based on the norm of the E-field. As can be seen in the comparison of FIGS. 14A and 14B, the part of the loop that contains the most useful EP information is accentuated and hence more meaningful OIS characteristics can be obtained from the weighted loop.

Figure 15B:
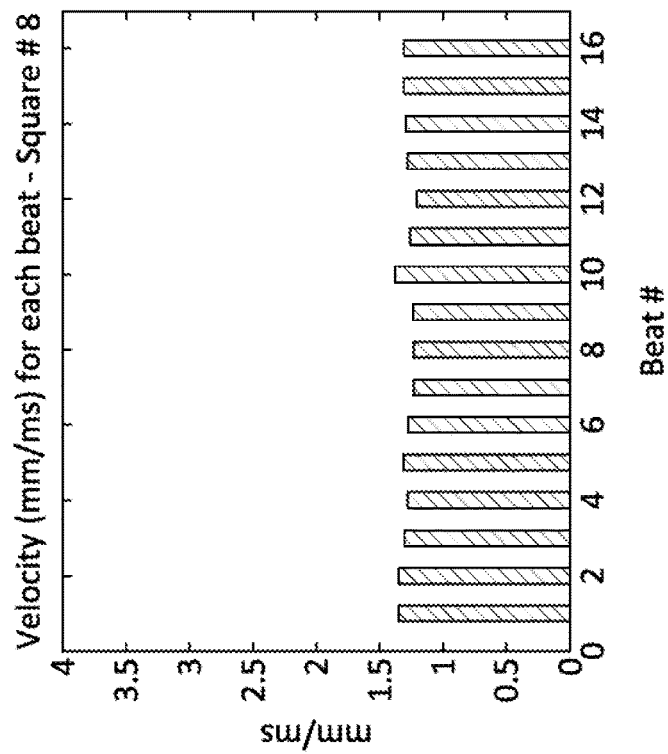
FIGS. 15A and 15B are graphs showing the conduction velocity estimated from two cliques over successive beats.
Figure 15A:
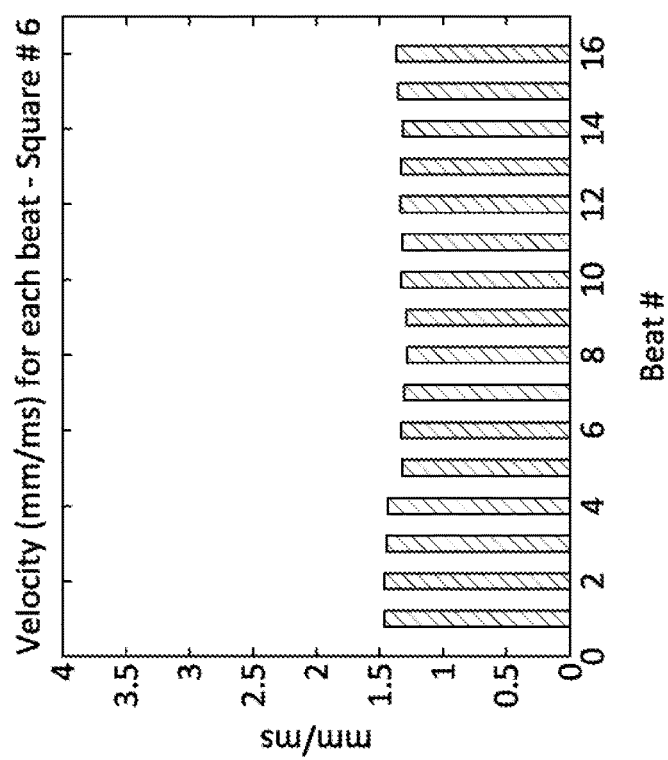

FIGS. 15A and 15B show the magnitude of conduction velocity estimated for successive beats on the RA septal wall for two different square cliques. FIG. 15A shows the magnitude of the conduction velocity for clique 6 and FIG. 15B shows the magnitude of the conduction velocity for clique 8. The velocity magnitude was estimated by taking the ratio of the peak-to-peak values of $\dot{\varphi}$ and $E_a$. The beat-to-beat variation in conduction velocity magnitude is minimal and the values of around 1.3 mm/ms are roughly what was expected. Conduction velocity magnitude and activation direction (unit vector) estimated for successive beats from the two adjacent cliques were as follows.

Clique #6
Velocity magnitude=1.35±0.06 mm/ms
Activation direction=(0.12, −0.91, 0.40)
Clique #8
Velocity magnitude=1.29±0.05 mm/ms
Activation direction=(0.10, −0.80, 0.58)

The activation direction and velocity calculated were similar and consistent with expected results in atrial tissue.

A split tip OIS catheter is also suitable for bipolar pacing in a manner that is much more tip localized than the conventional D-2 bipolar pacing and free of the concern over variable locational of capture (and variable thresholds) that can occur when the ring (and not the tip) captures myocardium. This is a great advantage when, for example, pacing is being done to establish lesion efficacy. The alternative, unipolar pacing, involves a distant electrode and thus is responsible for a large pacing artifact that complicates use of pacing for assessing blocks. The basic idea is that pacing is accomplished by assigning alternating polarities to the four tip electrodes. This may be accomplished by circuit elements such that the four electrograms and mapping system positions remain distinct and yet the tip appears as a "crossed bipole" from the standpoint of pacing. Alternatively this may be done by employing the stimulator, devoting two simultaneous channels to the four electrodes.

With each local depolarization, a new conduction velocity vector may be generated. The system can be configured to display various information including oriented arrow icons, Matlab quiver-like plots, and ripple maps. The system can further have the option to control the persistence of these direction and/or magnitude renderings. In one embodiment, the default process is to update immediately with each new local depolarization (that meets criteria for a depolarization).

Updates that visually replace prior visual assessments are sometimes preferred over cumulative multi-beat maps because if there is only modest movement of the catheter between repeated similar beats, the map will become cluttered with such representations. As a result, it can be beneficial to include a spatial density criterion (like that currently available with traditional mapping systems). New representation points would be added if none are within say 2 mm of previous points (and from the same mapped rhythm if that is distinguished). If old points lie within 2 mm of a new point, the new points can delete or hide old points. Particularly when playing back recorded segments and focus is on a region of interest where a multi-electrode mapping catheter is, the system can hide/delete prior representations at points in favor of the most recent cardiac cycle's representation since play back began.

In another embodiment, a variable persistence can be given to the point representations based on, a given number of milliseconds duration and observed during slow playback. The visual representations at points can come into existence and disappear in a manner that (similar to a propagation map available on the EnSite Velocity mapping system) suggests the wavefront itself (a region of typically 0.5-1 cm or so wide that encompasses the 5-10 ms or so of primary depolarization current and EGM generation). This can benefit the system by removing clutter and focusing attention on immediate events.

Transmural RF ablation possesses certain EGM characteristics which are exploitable by an orientation independent, OIS catheter electrode design and software. In particular, the unipolar signal (which to a first approximation is just a polarity inverted $E_n$ signal) may change from an rS pattern preablation to an r' pattern afterward. As a result, $E_n$ can change from a nice dominant upward deflection to a smaller downward deflection, perhaps a downward deflection that was present previously, but now appears minor in comparison with the upward deflection. This can reflect the fact that activation no longer propagates through the electrode clique but halts as it approaches.

While some implementations require a surface normal direction, n̂, to be supplied by a 3D mapping system's surface geometry model (based on the nearest surface point to a clique) this implementation can be less reliable in some circumstances. In one instance, using data from a 3D mapping system's surface geometry model can be less reliable when a cardiac surface curvature is high and thus imperfect surface models and small clique position errors can strongly influence the resulting n̂. The E field loop and traveling wave approach of OIS, however, can be used to generate n̂ and the other two OIS coordinates, â and ŵ, from EGMs alone. As a result, a live surface normal display can be determined. Such a surface normal can be a valuable reflection of catheter contact and wall distension and can even provide more detailed surface geometry models in the face of highly curved structures and respiratory or cardiac motion artifacts.

Figure 16:
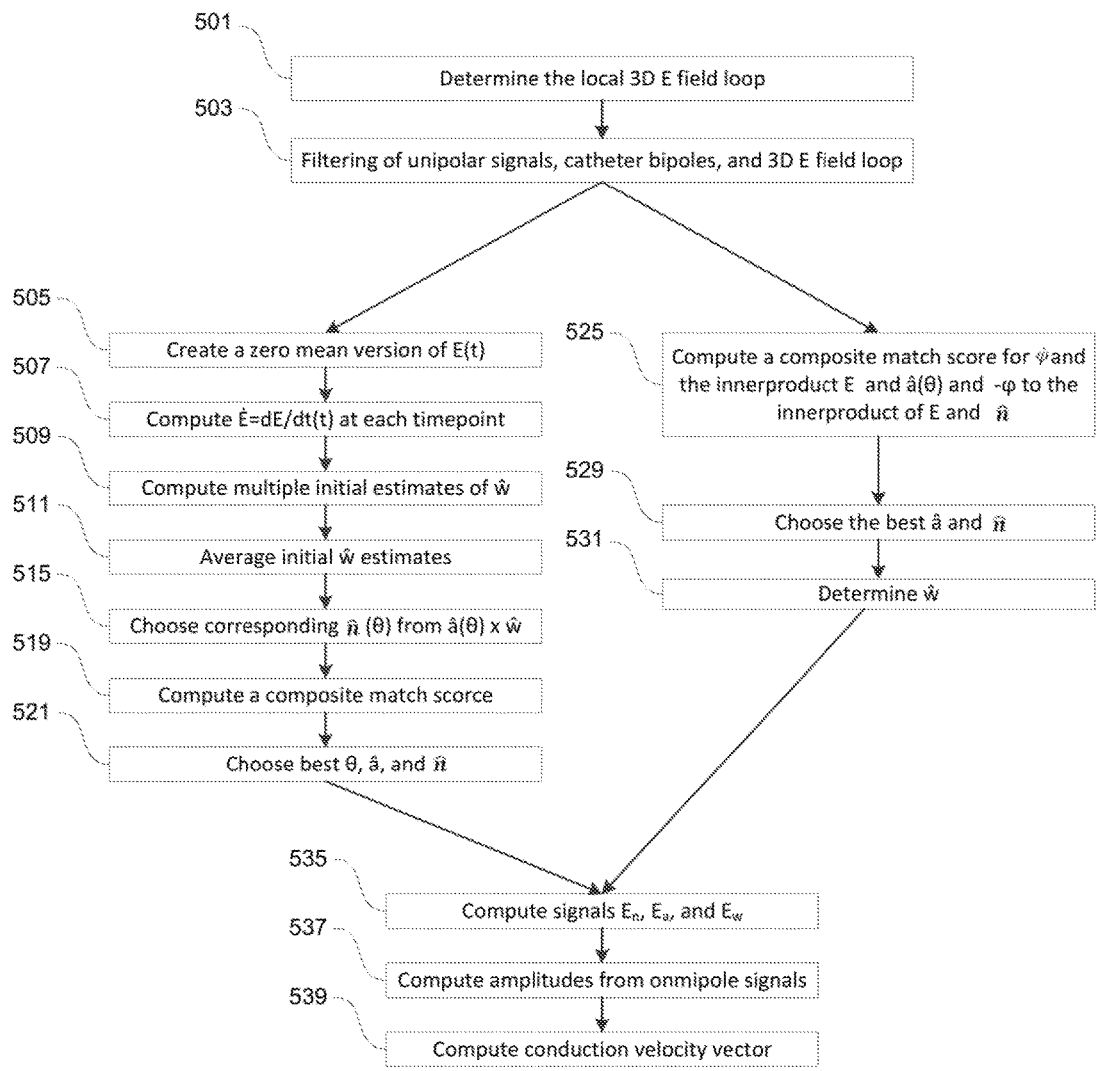
FIG. 16 is a flow diagram outlining the steps for obtaining an OIS coordinate frame.

FIG. 16 is a flow diagram outlining the steps for obtaining an OIS coordinate frame.

Step 501 comprises determining the local 3D electric field loop in the body or mapping system's coordinate frame. This step comprises having one or more electrode cliques on the cardiac surface and using a 3D mapping system to provide positions of electrodes comprising the clique and unipolar voltages obtained from the electrodes. From this information the 3D electric field loop can be determined.

Step 503 comprises matched filtering of all unipolar signals, catheter bipoles, and the resulting 3D E field loop. In another embodiment, for the purpose of OIS coordinate frame determinations and conduction velocity and activation direction, low or band pass filtering can be employed to create a more elliptical E field loop and thereby allow more consistent OIS coordinates as well as conduction velocity and activation direction determinations. Band pass filtering of 2-50 Hz can provide robust estimates of OIS coordinates, conduction velocity, and activation direction. In yet another embodiment, wideband filtering of E(t), e.g. 1-300 Hz, can be maintained for generating OIS signals $E_n$, $E_a$, and $E_w$ by the inner product of E(t) with n̂, â, and ŵ respectively to preserve EGM detail. In other embodiments, the filtering in step 503 can be performed in a different order than that shown in FIG. 16.

After step 503, there are two possible methods for determining â, n̂, and ŵ. If the system or user desires to first use ŵ then proceed to step 505. If the system or user desires to use â and n̂ first, then proceed to step 525.

Step 505 comprises creating a zero mean version of E(t) over the depolarization interval.

Step 507 comprises computing at each time point Ė=dE/dt(t).

Step 509 comprises computing an initial estimate of ŵ from the cross product of E and Ė at each time point.

Step 511 comprises averaging or weighted averaging the initial ŵ estimates over the depolarization interval for a best estimate of ŵ.

After ŵ has been estimated from step 511, the method next performs a 1-D search over angles θ for â and n̂ since â and n̂ have a proscribed 90 degree relationship to each other and both are perpendicular to ŵ. Only a half circle, θ(0-180 degrees), has to be searched as opposing directions will yield the negative in terms of match scores. A search can be performed on a suitably defined grid spacing. In one embodiment, every 2-3 degrees, for a total of only 60-90 evaluations. In other embodiments, other grid spacing can be defined by the system or user. Iterative search techniques may also be used but care can be taken to avoid local minima.

Step 515 comprises choosing the corresponding n̂ from the cross product â(θ)×ŵ(θ) for every â(θ).

Step 519 comprises computing a composite match score for how well φ matches $E_a(\theta)=E\cdot\hat{a}(\theta)$ (using an inner product) and how well -φ matches $E_n(\theta)=E\cdot(\theta)$ having determined n̂ from above.

Step 521 comprises choosing the best θ and thus the best â and n̂ from the previous steps.

In another embodiment, the method can skip computing Ė from step 507 and can instead perform a single cross product from a time point i with a sizable |E(t_i)|. This can be performed by letting A(t)=E(t)−mean(E(t)) be a zero mean version of the 3D E field trajectory. If A is assumed to be a 3×n matrix, form $(1/n)*A*A^T$ (this is a 3×3 positive definite covariance matrix). The SVD of this will yield singular values and vectors. The vector associated with the least singular value is ŵ (plus or minus a sign). Then check the loop's direction. The positive direction of ŵ "goes with the thumb using the right hand rule on the loop" and using the vector cross product between $A(t_i)$ and $A(t_{i+1})-A(t_i)$, ŵ's direction may be determined.

In another embodiment, the cross product or angular momentum can be used to determine ŵ. Let A(t)=E(t)−mean (E(t)). Over the loop points, compute the average cross product over the n time points A×Ȧ from the point-wise in time cross product of $A(t_i)$ with its time derivative $\dot{A}(t_i)$. Positive ŵ will be a normalized version of this vector. In another embodiment, the loop points can be weighted as discussed above and the average cross product computed as just described.

If the system or user desires to use â and n̂ first, the method proceeds from step 503 to step 525 and conducts either a 3 degree of freedom search to jointly solve for â and n̂ or begins with a 2D search over angles θ and ψ for either â or n̂. Only a hemisphere needs to be searched as opposing directions will yield the negative in terms of match scores. The search can be conducted on a defined grid spacing. Although increments of 2-3 degrees on latitude and longitude can work, this can lead to inefficient results as near the hemisphere's pole evaluations are much closer than 2-3 degrees. In one embodiment, a method employing some 10-20 fold fewer grid points can be used. Briefly, this uses an approximate solution to what is known as the Thompson Problem—distributing points evenly on a sphere. The approximate solution constructs lines of latitude, choosing points on successive lines rotated by $\pi(1-\varphi^{-3})$ radians where φ≅1.62. This method is more fully described in the '110 application, which is incorporated by reference above. Having determined â or n̂, the other may be found with a 1D semicircular search. Iterative search techniques can also be used but care taken to avoid local minima.

Step 525 comprises computing a composite match score for both how well φ matches the inner product of E and â and -φ matches the inner product of E and n̂.

Step 529 comprises choosing the best pair of â and n̂.

Step 531 comprises determining ŵ by the right hand rule and cross product ŵ=n̂×â.

In other embodiments, the method or system can proceed down both paths simultaneously and compare those results to determine the better fit. Whether proceeding down the path of using ŵ first, using n̂ and â first, or using both combined, the method then proceeds to step 535 to determine the standard final OIS information.

Step 535 comprises using the inner product of OIS coordinate directions with E field to compute the OIS omnipole signals $E_n$, $E_a$, and $E_w$. As discussed above, in one embodiment, the E-field from which omnipole signals are derived can be wide band filtered once the OIS coordinate frame has been determined from a low pass filtered E-field.

Step 537 comprises computing amplitudes from the omnipole signals. In one embodiment, the amplitudes are denoted $V_{pp}$ for peak-to-peak voltage and local activation timing denoted LAT.

Step 539 comprises computing the conduction velocity vector v which consists of the conduction velocity magnitude or speed (from the omnipole signals) times the activation direction a.

Figure 17:
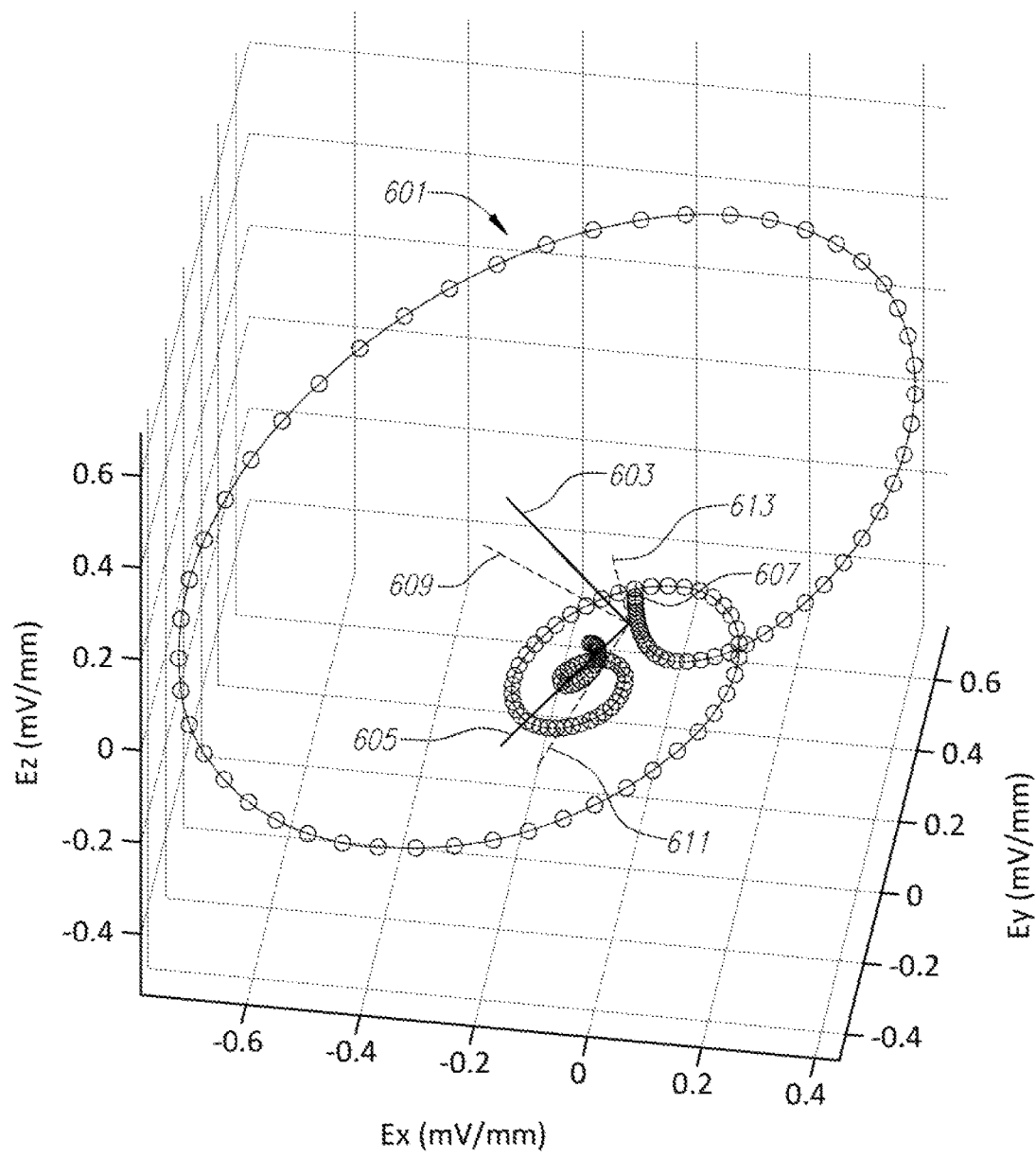
FIG. 17 is one embodiment of an E-field loop and OIS coordinates.

FIG. 17 illustrates an example of an E-field loop 601 and OIS coordinates. The 3D mapping system supplied a surface normal n̂ 603. The traditionally derived â 605 and traditionally derived ŵ 607 are determined by a process similar to that described in step 515. A loop derived OIS coordinate direction n̂ 609, a loop derived OIS coordinate direction â 611, and a loop derived OIS coordinate direction ŵ 613 are also shown in FIG. 17. In the illustrated embodiment, only minor readjustments were made to the coordinate frame. This minor adjustment reflects a high quality system supplied n̂.

A loop derived surface normal, n̂, opens up a number of potentially useful applications relating to cardiac EP mapping. One of the applications is assessing the adequacy of the existing local surface geometry model. A discrepancy between the derived information and the existing local surface geometry model can suggest additional geometry model acquisition is needed or in one embodiment can be automatically triggered. Another application is detecting a catheter force related surface distension. The catheter force related surface distension can be useful in the absence of a force sensor and can also be useful to suggest that the underlying geometry model has been temporarily altered. Another application of a loop derived surface normal is assessing the adequacy of local surface contact. Assessing the adequacy of local surface contact can benefit ablation formation and can also be used to reflect respiration and cardiac related motions that may not be well rendered by an existing 3D mapping system. Another application is allowing for a more robust surface geometry modeling in areas of highly curved cardiac structures and respiratory motion where other respiratory compensation may not always be effective at suppressing artifact and positional uncertainty. The above method can allow a user or system to recognize the situations described as the method responds in meaningful and reproducible ways as an OIS capable catheter is maneuvered throughout a vasculature or other body cavity or organ.

Figure 18A:
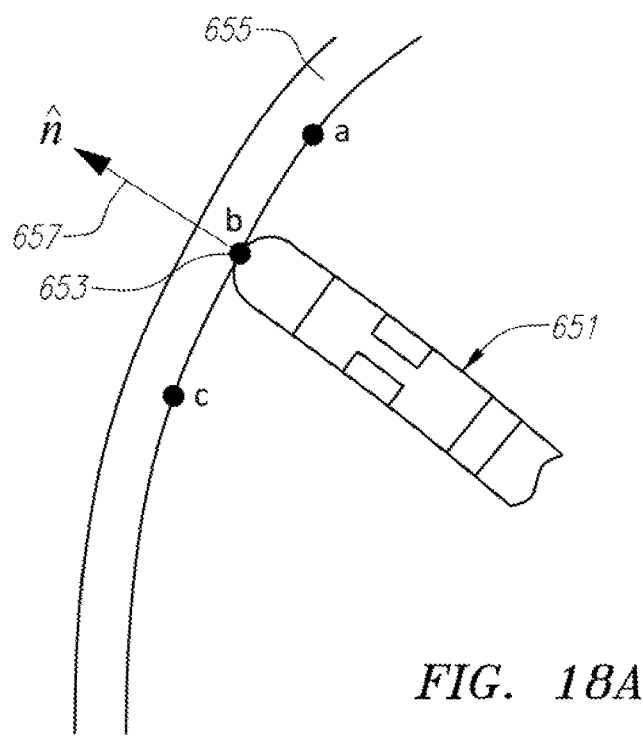
FIG. 18A is a side view of a catheter coming in contact with a tissue.
Figure 18B:
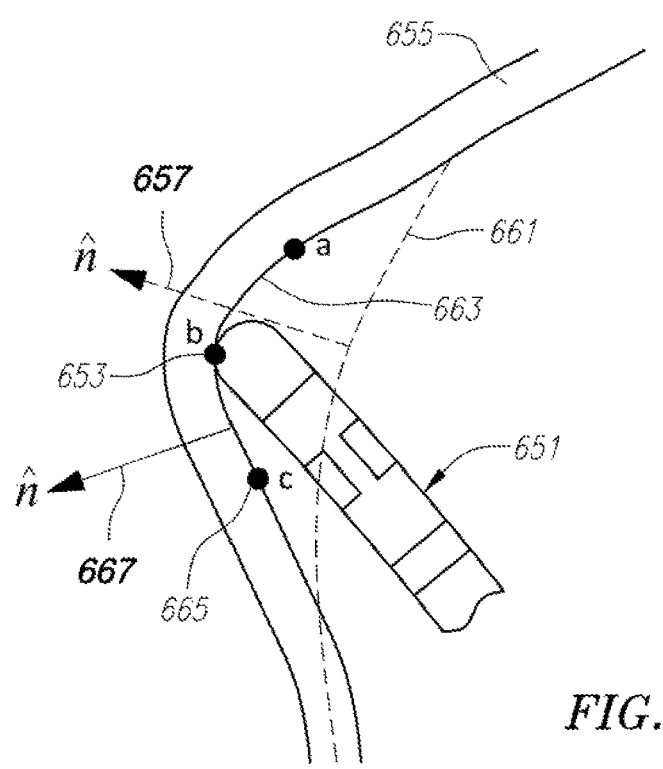
FIG. 18B is a side view of a catheter distending the tissue in FIG. 18A.

FIGS. 18A and 18B illustrate the application described above of detecting a catheter force related surface distension through a determination of the surface normal, n̂. n̂ is of interest itself to help with catheter positioning and to indicate the adequacy of a 3D mapping system surface geometry. It may also provide a real-time assessment of catheter force related distention of the endocardial or epicardial surface. This can be of particular use in the atria. FIG. 18A illustrates a catheter 651 placed at an initial contact point 653 of a myocardial wall 655. The catheter 651 is illustrated making contact with the myocardial wall 655, but not significantly distorting the shape of the myocardial wall 655. As a result, the surface normal 657 from both loop based means described above, and a 3D mapping system agree and are shown as n̂. FIG. 18B illustrates the catheter 651 being deflected and pushed into the myocardial wall 655. The catheter 651 is distending the endocardial surface from the original myocardial wall location 661 to a distended myocardial wall location 663. The 3D mapping system supplies surface normal 657 is the same as in FIG. 18A. The catheter clique's center however is now more accurately placed at a location between the initial contact point 653 and a second myocardial wall point 665. A proper surface normal 667, as determined through the above loop based method, is shown. By determining and using the proper surface normal 667 the system enables OIS signals $E_n$, $E_a$, and $E_w$ to be correctly resolved and thus the other results at the bottom of FIG. 16 can be correctly obtained. Further, the discrepancy between 3D mapping system supplied surface normal 657 and the proper surface normal 667 indicates an important surface distension. This surface distension can be undetectable using a standard 3D mapping system and can also often be unrecognizable on fluoro because of view angles, contrast, and shapes present in the fluoro system. Further, this can give a live n̂ display a potential role in lesion monitoring. A live display responding to force and local distension/deformation of the atrial wall can be used to enhance RF lesion quality if observed characteristic responses are seen in response to variations in tip deflection. One such characteristic can be a good degree of contact with the surface targeted for ablation. Surface normal information can inform a user of adequate contact and thus help to provide a sufficiently complete map geometry as well as static multibeat maps. As geometries may change during a procedure for real or artifact reasons, a recent discrepancy between an OIS loop derived n̂ and an n̂ from surface proximity could trigger a geometry and mapping update.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

What is claimed is:

1. A system for obtaining an OIS coordinate frame within a heart, comprising:
   a catheter comprising a plurality of closely spaced electrodes; and
   an electronic control unit configured to:
   receive a plurality of signals from the plurality of closely spaced electrodes;
   determine a local 3D electric field loop;
   create a zero mean version of E(t) over a depolarization interval;
   compute an Ė value at each of a plurality of time intervals;
   compute an initial estimate of ŵ from a cross product of E and the Ė value for each of the plurality of time intervals;
   average the initial estimate of ŵ from each of the plurality of time for an estimate of ŵ;
   determine a plurality of â(θ) values and choosing a corresponding n̂(θ) value for each of the plurality of â(θ) values;
   compute a composite match score; and
   choose at least one value for â and a value for n̂
   outputting at least one of the estimate of ŵ and at least one value for â and a value for n̂.

2. The system of claim 1, wherein the electronic control unit is further configured to compute at least one of OIS omnipole signals comprising $E_n$, $E_a$, and $E_w$.

3. The system of claim 2, wherein the electronic control unit is further configured to compute at least one amplitude from the at least one OIS omnipole signals.

4. The system of claim 3, wherein the electronic control unit is further configured to compute a conduction velocity vector from the at least one OIS omnipole signals and the at least one amplitude.

5. The system according to claim 1, wherein the electronic control unit is further configured to filter all of a plurality of unipolar signals, a plurality of catheter bipoles, and the 3D E-field loop before determining the local 3D electric field loop and the OIS coordinate fame of $\hat{n}$, $\hat{a}$, and $\hat{w}$.

6. The system according to claim 1, wherein the electronic control unit is further configured to determine a catheter force related surface distension through the value for $\hat{n}$.

7. The system according to claim 1, wherein the electronic control unit is further configured to determine whether a high quality OIS signal is present within the local 3D electric field loop.

8. The system according to claim 1, wherein the electronic control unit is further configured to weight a plurality of points within the local 3D electric field loop.

9. A method for obtaining an OIS coordinate frame within a heart, comprising:
   receiving a plurality of signals from a plurality of closely spaced electrodes
   determining a local 3D electric field loop;
   creating a zero mean version of E(t) over a depolarization interval;
   computing an $\dot{E}$ value at each of a plurality of time intervals;
   computing an initial estimate of $\hat{w}$ from a cross product of E and the $\dot{E}$ value for each of the plurality of time intervals;
   averaging the initial estimate of $\hat{w}$ from each of the plurality of time for an estimate of $\hat{w}$;
   determining a plurality of $\hat{a}(\theta)$ values and choosing a corresponding $\hat{n}(\theta)$ value for each of the plurality of $\hat{a}(\theta)$ values;
   computing a composite match score; and
   choosing at least one value for $\hat{a}$ and a value for $\hat{n}$.

10. The method of claim 9, further comprising computing at least one of OIS omnipole signals comprising $E_n$, $E_a$, and $E_w$.

11. The method of claim 10, further comprising computing at least one amplitude from the at least one OIS omnipole signals.

12. The method of claim 11, further comprising computing a conduction velocity vector from the at least one OIS omnipole signals and the at least one amplitude.

13. The method according to claim 9, further comprising filtering all of a plurality of unipolar signals, a plurality of catheter bipoles, and the 3D E-field loop before determining the local 3D electric field loop.

14. The method according to claim 9, wherein the electronic control unit is further configured to determine a catheter force related surface distension through the value for $\hat{n}$.

15. The method according to claim 9, wherein the electronic control unit is further configured to determine whether a high quality OIS signal is present within the local 3D electric field loop.

16. A system for obtaining an OIS coordinate frame within a heart, comprising:
   a catheter comprising a plurality of closely spaced electrodes; and
   an electronic control unit configured to:
   receive a plurality of signals from the plurality of closely spaced electrodes;
   determine a local 3D electric field loop;
   compute a composite match score for how well $\hat{\varphi}$ matches an inner product of E and $\hat{a}(\theta)$ and $-\varphi$ matches an inner product of E and $\hat{n}$;
   choose a value for $\hat{a}$ and a value for $\hat{n}$; and
   determine a value for $\hat{w}$ by a right hand rule and a cross product $\hat{w}=\hat{n}\times\hat{a}$
   outputting at least one of the value for $\hat{w}$ and the value for $\hat{a}$ and a value for $\hat{n}$.

17. The system of claim 16, wherein the electronic control unit is further configured to compute at least one of OIS omnipole signals comprising $E_n$, $E_a$, and $E_w$.

18. The system of claim 17, wherein the electronic control unit is further configured to compute at least one amplitude from the at least one OIS omnipole signals.

19. The system of claim 18, wherein the electronic control unit is further configured to compute a conduction velocity vector from the at least one OIS omnipole signals and the at least one amplitude.

20. The system according to claim 16, wherein the electronic control unit is further configured to filter all of a plurality of unipolar signals, a plurality of catheter bipoles, and the 3D E-field loop before determining the local 3D electric field loop.

* * * * *